United States Patent
Quagliato et al.

(10) Patent No.: US 6,458,817 B1
(45) Date of Patent: Oct. 1, 2002

(54) SUBSTITUTED ARYLSULFIDES, ARYLSULFOXIDES AND ARYLSULFONES AS BETA-3 ADRENERGIC RECEPTOR AGONISTS

(75) Inventors: Dominick Anthony Quagliato, Bridgewater; Patrick Michael Andrae, New Brunswick, both of NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 09/903,802

(22) Filed: Jul. 12, 2001

Related U.S. Application Data

(60) Provisional application No. 60/218,763, filed on Jul. 17, 2000.

(51) Int. Cl.$^7$ .................. C07D 271/06; A01K 31/4245
(52) U.S. Cl. ................... 514/364; 548/131; 564/363
(58) Field of Search ............... 564/363; 548/131; 514/364

(56) References Cited

U.S. PATENT DOCUMENTS

| | | | |
|---|---|---|---|
| 4,622,342 A | * 11/1986 | Cantello | ........ 514/653 |
| 5,561,142 A | 10/1996 | Fisher et al. | |
| 5,578,620 A | 11/1996 | Fujita et al. | |
| 5,614,523 A | 3/1997 | Audia et al. | |
| 5,741,789 A | 4/1998 | Hibschman | |
| 5,786,356 A | 7/1998 | Bell et al. | |
| 5,789,402 A | 8/1998 | Audia et al. | |
| 6,069,176 A | 5/2000 | Tsuchiya et al. | |

FOREIGN PATENT DOCUMENTS

| | | |
|---|---|---|
| EP | 0 089 154 A2 | 9/1983 |
| EP | 0 449 261 A1 | 10/1991 |
| EP | 0 659 737 A2 | 6/1995 |
| EP | 0 714 883 A1 | 6/1996 |
| EP | 0 764 640 A1 | 3/1997 |
| WO | WO 99/65895 | 12/1999 |
| WO | WO 01/17989 A2 | 3/2001 |
| WO | WO 01/44227 A1 | 6/2001 |

OTHER PUBLICATIONS

Marc S. Berridge et al., Nucl. Med. Biol., 1992, 563–569, 19(5).
Joan M Caroon et al., J. Pharm. Sci., Jan. 1987, 32–34, 76(1).
A. Guy et al., Synthesis, Sep. 1992, 821–22.
Manabu Hori et al., J. Org. Chem., 1998, 889–894, 63.
Yunsheng Huang et al., J. Med. Chem., 1998, 2361–2370, 41.
Bernard Hulin et al., J. Med. Chem., 1992, 1853–1864, 35.
Carl Kaiser et al., J. Med. Chem., 1977, 687–692, 20(5).
Yutaka Kawashima et al., Chem. Pharm. Bull, 1995, 1132–1136, 43(7).
Kiyoto Koguro et al., Synthesis, 1998, 910–914.
Gerard LeClerc et al., J. Med. Chem., 1980, 738–744, 23(7).
D. Mauleon et al., Il Farmaco, 1989, 1109–1117, 44(11).
Alexander McKillop et al., J. Am. Chem. Soc., Sep. 1971, 4919–4920, 93(19).
Ricardo Tapia et al., Synthetic Communications, 1986, 681–687, 16(6).
Edward C. Taylor et al., Synthesis, Aug. 1981, 606–608.
Michiaki Tominaga et al., Chem. Pharm. Bull, 1987, 3699–3704, 35(9).
R.H. Uloth et al., J. Med. Chem., 1966, 88–97, 9.
Paul C. Unangst et al., J. Med. Chem., 1994, 322–328, 37.
Sophie Vanwetswinkel et al., J. Antibiotics, Sep. 1994, 1041–1051, 47(9).
S. Tamada et al., JP 01061468 A2 (English abstract), 1989.

\* cited by examiner

*Primary Examiner*—Robert Gerstl
(74) *Attorney, Agent, or Firm*—Arnold S. Milowsky

(57) ABSTRACT

This invention provides compounds of Formula I having the structure

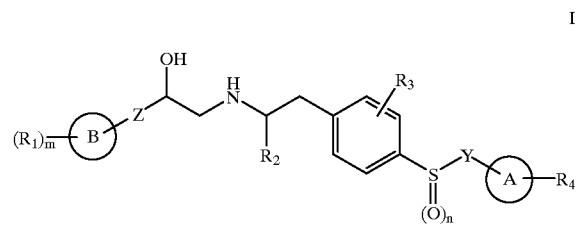

wherein $R_1$, $R_2$, $R_3$, $R_4$, $R_5$, $R_6$, Y, Z, m, n,

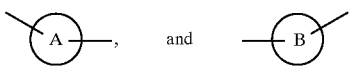

and are as defined hereinbefore or a pharmaceutically acceptable salt thereof, which are useful in treating or inhibiting metabolic disorders related to insulin resistance or hyperglycemia (typically associated with obesity or glucose intolerance), atherosclerosis, gastrointestinal disorders, neurogenetic inflammation, glaucoma, ocular hypertension and frequent urination; and are particularly useful in the treatment or inhibition of type II diabetes.

10 Claims, No Drawings

SUBSTITUTED ARYLSULFIDES, ARYLSULFOXIDES AND ARYLSULFONES AS BETA-3 ADRENERGIC RECEPTOR AGONISTS

This application claims the benefit of U.S. Provisional Application No. 60/218,763, filed Jul. 17, 2000.

BACKGROUND OF THE INVENTION

This invention relates to arylsulfide, arylsulfoxide and arylsulfone derivatives which are $\beta_3$ adrenergic receptor agonists useful for the treatment of metabolic disorders related to insulin resistance or hyperglycemia (typically associated with obesity or glucose intolerance), atherosclerosis, gastrointestinal disorders, neurogenetic inflammation, glaucoma, ocular hypertension, and and frequent urination, and are particularly useful in the treatment or inhibition of type II diabetes.

The subdivision of $\beta$ adrenergic receptors ($\beta$-AR) into $\beta_1$- and $\beta_2$-AR has led to the development of $\beta_1$- and $\beta_2$-antagonists and/or agonists which have been useful for the treatment of cardiovascular disease and asthma. The recent discovery of "atypical" receptors, later called $\beta_3$-AR, has led to the development of $\beta_3$-AR agonists which may be potentially useful as antiobesity and antidiabetic agents. For recent reviews on $\beta_3$-AR agnoists , see: 1. A. D. Strosberg, *Annu. Rev. Pharmacol. Toxicol.* 1997, 37, 421; 2. A. E. Weber,*Ann. Rep. Med. Chem.* 1998, 33, 193; 3. C. P. Kordik and A. B. Reitz, *J. Med. Chem.* 1999, 42, 181; 4. C. Weyer, J. F. Gautier and E. Danforth, *Diabetes and Metabolism,* 1999, 25, 11.

Compounds that are potent and selective $\beta_3$ agonists, may be potentially useful antiobesity agents. Low levels or lack of $\beta_1$ and $\beta_2$-agonistic properties will minimize or eliminate the adverse side effects that are associated with $\beta_1$ and $\beta_2$ agonistic activities, i.e. increased heart rate, and muscle tremor, respectively.

Early developments in the $\beta_3$-agonist field are described in European patent 427480, U.S. Pat. Nos. 4,396,627, 4,478, 849, 4,999,377, 5,153,210. Although the early developments purport to claim compounds with greater $\beta_3$-AR selectivity over the $\beta_1$- and $\beta_2$-AR. However, clinical trials in humans with those early developed $\beta_3$-agonists have, so far, not been successful.

More recently, potent and selective human $\beta_3$ agonists have been described in several patents and published applications: WO 98/32753, WO 97/46556, WO 97/37646, WO 97/15549, WO 97/25311, WO 96/16938, WO 95/29159, European Patents 659737, 801060, 714883, 764640, 827746, and U.S. Pat. Nos. 5,561,142, 5,705,515, 5,436, 257, and 5578620. These compounds were evaluated in Chinese hamster ovary (CHO) cells test procedures, expressing cloned human β3 receptors, which predict the effects that can be expected in humans (Granneman et al., *Mol Pharmacol.*, 1992, 42, 964; Emorine et al., *Science,* 1989, 245, 1118; Liggett *Mol. Pharmacol.*, 1992, 42, 634).

$\beta_3$-Adrenergic agonists also are useful in controlling the frequent urge of urination. It has been known that relaxation of the bladder detrusor is under beta adrenergic control (Li J H, Yasay G D and Kau S T *Pharmacology* 1992; 44: 13–18). Beta-adrenoceptor subtypes are in the detrusor of guinea-pig urinary bladder. Recently, a number of laboratories have provided experimental evidence of $\beta_3$ adrenergic receptors in a number of animal species including human (Yamazaki Y, Takeda H, Akahane M, Igawa Y, et al. *Br. J. Pharmacol.* 1998; 124: 593–599), and that activation of the $\beta_3$ receptor subtype by norepinephrine is responsible for relaxation of the urinary bladder.

Urge urinary incontinence is characterized by abnormal spontaneous bladder contractions that can be unrelated to bladder urine volume. Urge urinary incontinence is often referred to hyperactive or unstable bladder. Several etiologies exist and fall into two major categories, myogenic and neurogenic. The myogenic bladder is usually associated with detrusor hypertrophy secondary to bladder outlet obstruction, or with chronic urinary tract infection. Neurogenic bladders are associated with an uninhibited micturition reflex. An upper motor neuron disease is usually the underlying cause. In either case, the disease is characterized my abnormal spontaneous contractions that result in an abnormal sense of urinary urgency and involuntary urine loss. At present, the most common therapy for hyperactive bladder includes the use of antimuscarinic agents to block the action of the excitatory neurotransmitter acetylcholine. While effective in neurogenic bladders, their utility in myogenic bladders is questionable. In addition, due to severe dry mouth side-effects associated with antimuscarinic therapy, the patient compliance with these agents is only approximately 30%.

In the bladder, $\beta_3$ adrenergic receptor agonists activate adenylyl cyclase and generate cAMP through the G-protein coupled $\beta_3$ receptor. The resulting phosphorylation of phospholamban/calcium ATPase enhances uptake of calcium into the sarcoplasmic reticulum. The decrease in intracellular calcium inhibits bladder smooth muscle contractility.

It is suggested therefore, that activation of the $\beta_3$ adrenergic receptor in the urinary bladder will inhibit abnormal spontaneous bladder contractions and be useful for the treatment of bladder hyperactivity. Note, that unlike the antimuscarinics, $\beta_3$ adrenergic receptor agonists would be expected to be active against both neurogenic and myogenic etiologies.

Despite all these recent developments there is still no single therapy available for the treatment of type II diabetes (NIDDM), obesity, atherosclerosis, gastrointestinal disorders, neurogenetic inflammation, frequent urination and related diseases. A potent and selective $\beta_3$ adrenergic receptor agonist is therefore highly desirable for the potential treatment of such disease states.

DESCRIPTION OF THE INVENTION

This invention provides compounds of Formula I having the structure

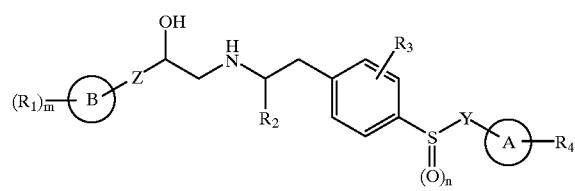

wherein,

R$_1$ is hydrogen, alkyl of 1–6 carbon atoms, halogen, trifluoromethyl, trifluoromethoxy, alkoxy of 1–6 carbon atoms, hydroxy, nitro, amino, cyano, carboxy, alkoxycarbonyl of 2–7 carbon atoms, aminocarbonyl, alkylamino of 1–6 carbon atoms, dialkylamino of 1–6 carbon atoms per alkyl group, acyl of 2–7 carbon atoms, acylamino of 2–7 carbon atoms, amino, phenylalkyl having 1–6 carbon atoms in the alkyl moiety, or —NR$_5$SO$_2$R$_5$;

R$_2$ is hydrogen, or alkyl of 1–6 carbon atoms;

R$_3$ is hydrogen, alkyl of 1–6 carbon atoms, alkoxy of 1–6 carbon atoms, or halogen;

R$_4$ is (a) a 5–6 membered heterocyclic ring having 1–4 heteroatoms selected from O, S, and N, optionally substituted with R$_6$; (b) a phenyl ring optionally substituted with R$_6$; (c) phenylalkyl having 1–6 carbon atoms in the alkyl moiety; or (d) alkyl of 1–6 carbon atoms;

R$_5$ is hydrogen, alkyl of 1–6 carbon atoms, or phenyl;

R$_6$ is alkyl of 1–6 carbon atoms, halogen, trifluoromethyl, trifluoromethoxy, alkoxy of 1–6 carbon atoms, hydroxy, nitro, amino, cyano, aminocarbonyl, alkylamino of 1–6 carbon atoms, dialkylamino of 1–6 carbon atoms per alkyl group, acyl 2–7 carbon atoms, acymino of 2–7 carbon atoms, amirno, phenylalkyl having 1–6 carbon atoms in the alkyl moiety, —CO$_2$R$_5$, or —NR$_5$SO$_2$R$_5$; or is a 5–6 heterocyclic ring having 1–4 heteroatoms selected from O, S, and N mono- or di- substituted with R$_2$;

is
(a) a 5–6 membered heterocyclic ring having 1–4 heteroatoms selected from O, N, and S; or
(b) a phenyl ring;

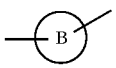

is
(a) a phenyl ring; or
(b) a phenyl fused to a 5–6 membered heterocyclic ring having 1–4 heteroatoms selected from O, N, and S;

Y is alkyl of 1–6 carbon atoms;

Z is a bond, or —OCH$_2$—;

m is 1–2;

n is 0–2;

or a pharmaceutically acceptable salt thereof, which are selective agonists at human β$_3$ adrenergic receptors and are useful in treating or inhibiting metabolic disorders related to insulin resistance or hyperglycemia (typically associated with obesity or glucose intolerance), atherosclerosis, gastrointestinal disorders, neurogenetic inflammation, glaucoma, ocular hypertension, and frequent urination; and are particularly useful in the treatment or inhibition of type II diabetes.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable aids when a compound of this invention contains a basic moiety. Salts may also be formed from organic and inorganic bases, such as alkali metal salts (for example, sodium, lithium, or potassium) alkaline earth metal salts, ammonium salts, alkylammonium salts containing 1–6 carbon atoms or dialkylammonium salts containing 1–6 carbon atoms in each alkyl group, and trialkylammonium salts containing 1–6 carbon atoms in each alkyl group, when a compound of this invention contains an acidic moiety.

Alkyl includes both straight chain as well as branched moieties. By definition alkyl also includes alkyl moieties which are optionally mono- or poly substituted with groups such as halogen, hydroxy, cyano, alkoxy, aryloxy, arylalkyl, alkylthio, arylthio, amino, alkylamino, and dialkylamino. Halogen means bromine, chlorine, fluorine, and iodine.

As used herein, a heterocyclic ring is a ring contining 1–4 heteroatoms selected from N, O, and S, which may be saturated, unstaturated, or partially unsaturated. It is understood that the heterocyclic ring does not contain heteroatoms in arrangements which would make them inherently unstable. For example, the term heterocyclic ring does not include ring systems containing O—O bonds in the ring backbone. Preferred heterocycles and phenyl fused heterocycles include, but are not limited to, pyridyl, pyrimidinyl, pyrrolyl, piperidinyl, piperazinyl, thienyl, imidazolyl, thiazolyl, benzimidazolyl, benzotriazolyl, benzothiadiazolyl, oxadiazolyl, indolyl, benzofuranyl, dihydrobenzofuranyl, and methylenedioxyphenyl. More preferred heterocycles include oxadiazolyl, and isoxazolyl, and more preferred phenyl fused heterocycles include benzotriazolyl.

When B is a phenyl fused heterocycle, either ring of the phenyl fused heterocycle may be bonded to Z, and either ring may contain the R$_1$ substitutent. When B contains more than one R$_1$ group, they may be the same or different. Similarly, when R$_6$ is —NR$_5$SO$_2$R$_5$, the R$_5$ substituents may be the same or different.

The compounds of the present invention contain at least one asymmetric center. Additional asymmetric centers may exist on the molecule depending upon the structure of the substituents on the molecule. The compounds may be prepared as a racemic mixture and can be used as such, or may be resolved into the. In addition to covering the racemic compounds, this invention also covers all individual isomers, enantiomers, diasteromers or mixtures thereof, regardless of whether the structural representations of the compounds indicate such stereochemistry.

Preferred compounds of Formula I are those in which
R$_1$ is hydrogen, alkyl of 1–6 carbon atoms, halogen, trifluoromethoxy, alkoxy of 1–6 carbon atoms, hydroxy, cyano, or —NR$_5$SO$_2$R$_5$;

R$_3$ is hydrogen;

R$_6$ is alkyl of 1–6 carbon atoms, alkoxy of 1–6 carbon atoms, or is a 5–6 membered heterocyclic ring having 1–4 heteroatoms selected from O, S, and N mono- or di- substituted with R$_2$;

Y is methylene;

or a pharmaceutically acceptable salt thereof.

Specifically preferred compounds of this invention are:
a) 4-(4-{2-[(2S)-3-(1H-Benzotriazol-4-yloxy)-2-hydroxy-propylamino]-ethyl}-phenylsulfanylmethyl)-benzonitrile;
b) (2S)-1-(1H-Benzotriazol-4-yloxy)-3-{2-[4-(3-p-tolyl-[1,2,4]oxadiazol-5-ylmethylsulanyl)-phenyl]-ethylamino}-propan-2-ol;
c) 4-(3-{2-[4-(5-tert-Butyl-[1,2,4]oxadiazol-3-ylmethylsulfanyl)-phenyl]-ethylamino}-2-hydroxy-propoxy)-phenol;
d) 4-[(2S)-3-(2-{4-[5-(3,5-Dimethyl-isoxazol-4-yl)-[1,2,4]oxadiazol-3-ylmethanesulfonyl]-phenyl}-ethylamino)-2-hydroxy-propoxy]-phenol;
e) 4-((2S)-3-{2-[4-(5-tert-Butyl-[1,2,4]oxadiazol-3-ylmethanesulfonyl)-phenyl]-ethylamino}-2-hydroxy-propoxy)-phenol;
f) 4-[(2S)-2-Hydroxy-3-(2-{4-[5-(4-methoxy-phenyl)-[1,2,4]oxadiazol-3-ylmethylsulanyl]-phenyl}-ethylamino)-propoxy]-phenol;

g) 4-[(2S)-2-Hydroxy-3-(2-{4-[5-(4-methoxy-phenyl)-[1,2,4]oxadiazol-3-ylmethylsulanyl]-phenyl}-ethylamino)-propoxy]-2-methyl-phenol;

h) 4-((2S)-3-{2-[4-(5-Benzyl-[1,2,4]oxadiazol-3-ylmethanesulfinyl)-phenyl]-ethylamino}-2-hydroxy-propoxy)-phenol;

i) 2-[(4-{[(5-phenyl-1,2,4-oxadiazol-3-yl)methyl]sulfonyl}phenethyl)amino]-1-[4-(trifluoromethoxy)phenyl]-1-ethanol; and j) N-[2-hydroxy-5-((1 R)-1-hydroxy-2-{[4-({[5-(4-methoxyphenyl)-1,2,4-oxadiazol-3-yl]methyl}sulfonyl)phenethyl]amino}ethyl)phenyl]methane sulfonamide or a pharmaceutically acceptable salt thereof.

The compounds of this invention were be prepared according to the following schemes from commercially available starting materials or starting materials which can be prepared using literature procedures. These schemes show the preparation of representative compounds of this invention. The compounds of Formula(I) of the instant invention can be prepared from a reaction between epoxide intermediates, such as those of Formula (II), and amine intermediates, such as those of formula (III). The preparation of these intermediates is described in the following schemes.

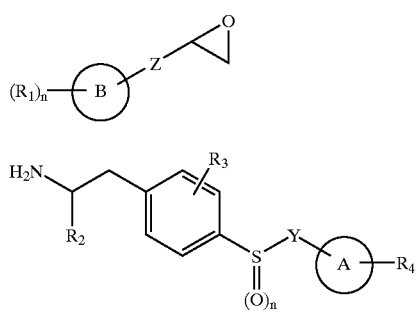

where n, Z, Y, A, B, $R_1$, $R_2$, $R_3$, and $R_4$, are as defined under Formula (I).

Compounds of Formula (II) are known in the literature or may be prepared by a variety of methods familiar to those skilled in the art of organic synthesis. One common route is illustrated in Scheme 1. Aldehyde 1, which is commercially available or prepared using methods available in the literature, is treated with sodium trimethylsulfoxonium ylide (made by treating trimethylsulfoxonium iodide with sodium hydride) in a solvent such as THF. The reaction mixture is processed and purified to afford the epoxide 2.

SCHEME 1

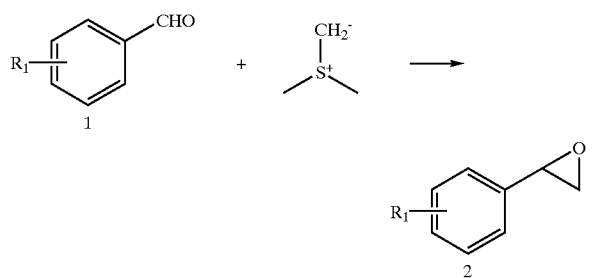

Another common route to compounds of Formula (II) is illustrated in Scheme 2. Phenol 3, which is commercially available or prepared using methods available in the literature, is treated with R(+)-glycidol, triphenylphosphine, and finally diethylazodicaboxylate. These conditions are commonly known, in the art, as Mitsunobu conditions. The reaction mixture is processed and purified to afford the epoxide 4. $R_1$ substituents as well as others may need to be protected during the above or subsequent procedures. A description of the use of such protecting groups may be found in *Protecting Groups in Organic Synthesis*, 2$^{nd}$ Ed., T. W. Greene and P. G. M. Wuts, John Wiley and Sons, New York, 1991.

SCHEME 2

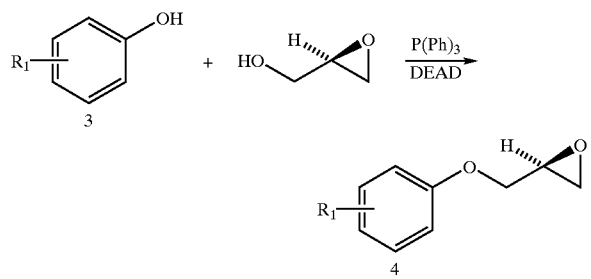

An alternative method that may be used to prepare compounds of Formula (II) is illustrated in Scheme 3. Phenol 3a, which is commercially available or prepared using methods available in the literature, is treated with a base, such as potassium carbonate, and (2S)-(+)-glycidyl-3-nitrobenzenesulfonate in a polar aprotic solvent, such as 2-butanone, at reflux. Standard purification procedures afford the epoxide 4a.

SCHEME 3

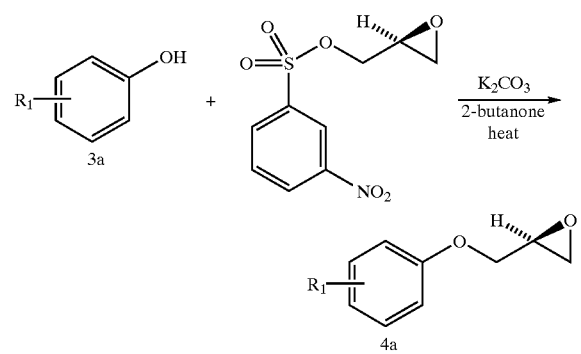

A class of compounds of Formula(IIb) that are functionally equivalent to epoxides but contain no 3-membered oxirane can be prepared by a variety of methods familiar to those skilled in the art. One route is shown in Scheme 4. This is substantially the same procedure described by E. J. Corey and J. O. Link, J. Org. Chem., 56, 442, (1991). The methyl ketone 5, available commercially or readily prepared by methods described in the literature, is treated with copper(II) bromide or dioxane/bromine to give the α-bromoketone 6. This is then asymmetrically reduced using chiral reducing agents, such as, (R) or (S)-Alpine borane or (R) or (S)-tetrahydro-1-methyl-3,3-diphenyl-1H,3H-pyrolo[1,2-c][1,3,2]oxazaborole-borane to afford the chiral alcohol 7. This alcohol group can then be protected most conveniently by a silicon based reagent, such as, triethylsilyl chloride; or the bromine can be replaced by the more reactive iodine by treating compound 7 with sodium iodide. This iodo-hydrin 8 can be O-protected using the same procedure as is used for compound 7 to afford compounds of Formula (IIb).

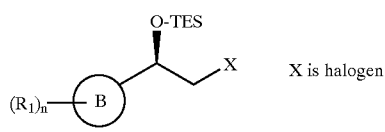

SCHEME 4

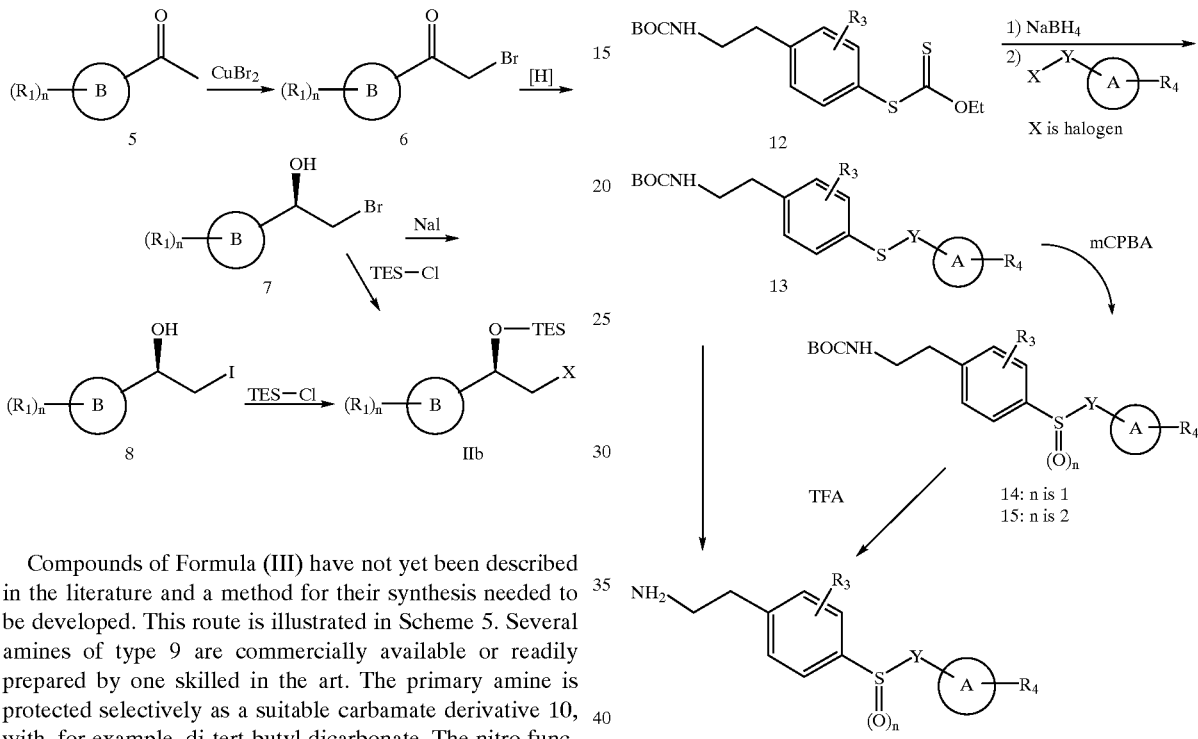

Compounds of Formula (III) have not yet been described in the literature and a method for their synthesis needed to be developed. This route is illustrated in Scheme 5. Several amines of type 9 are commercially available or readily prepared by one skilled in the art. The primary amine is protected selectively as a suitable carbamate derivative 10, with, for example, di-tert-butyl dicarbonate. The nitro functional group is reduced using catalytic hydrogenation conditions, such as 5% Pd/C and $H_2$ gas, to provide the aniline 11. The primary aromatic amine group is transformed into a diazonium group by treatment with sodium nitrite in cold hydrochloric acid. The diazonium salt is not isolated but treated immediately with potassium ethyl xanthate in aqueous sodium bicarbonate to afford the aromatic xanthate 12. This xanthate 12 is then treated with sodium borohydride followed by an alkylating agent, such as, benzyl bromide to give the sulfide 13. This material may be treated with mCPBA to afford either the sulfoxide or the sulfone. One molar equivalent of mCPBA forms a sulfoxide 14; two molar equivalents of mCPBA form the sulfone 15. Deprotection of the amine with an acid, such as trifluoroacetic acid, affords the desired intermediates of Formula (III).

SCHEME 5

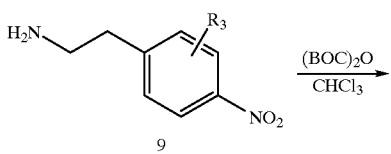

Compounds of Formula (III) where $R_2$ is methyl can be prepared from phenylalanine as illustrated in Scheme 6. It is possible to use one of the known methods of reducing an amino acid to an α-methyl amine. See B. G. Donner, Tetrahedron Lett., 36(8), pp. 1223–1226; or J. D. Bloom, et. al., J. Med. Chem., 35, pp. 3081–3084 (1992). Preferably, we developed our own method for reducing the amino acid to α-methyl amines. Following the reduction, nitration via electrophilic aromatic substitutions affords the aromatic nitro compound 16. See Advanced Organic Chemistry, b 4th Ed., J. March, John Wiley & Sons, New York, 1992. Then by further electrophilic aromatic substitution the $R_3$ group is introduced into the position meta to the nitro group, 17a. If the $R_3$ group is to be ortho to the nitro group, 17b, the nitro group is reduced and acylated, then treated with butyllithium followed by the electrophile $R_3$-X to afford the desired compound. See V. Snieckus, Bull. Soc. Chim. France, 1988, N° 1, pp. 67–78. Reduction of the nitro compound 17a or hydrolysis of the amide 17b gives the compound 11a, which can be carried on to compounds of Formula (III), as shown in Scheme 6.

SCHEME 6

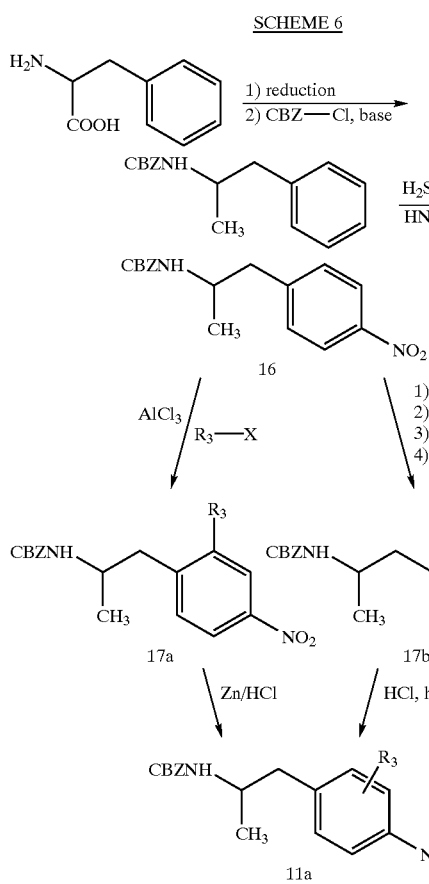

SCHEME 7

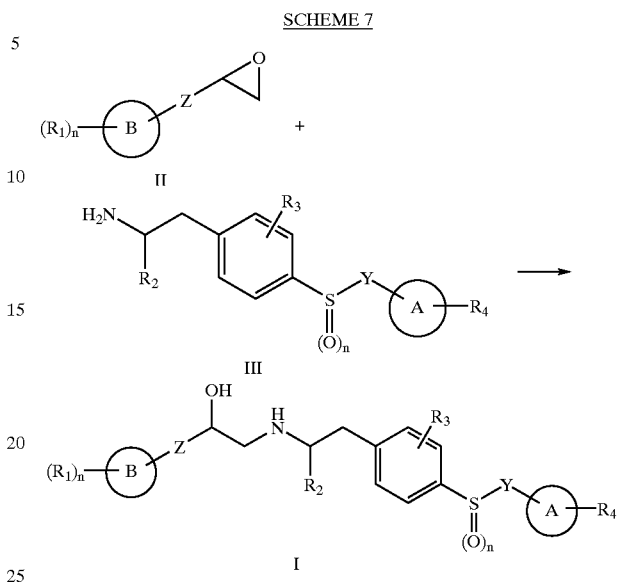

methanol and THF at 50° C. for 48 hours. This procedure is illustrated in Scheme 7.

If a deprotection step is necessary it can immediately follow the coupling step just described.

In the examples where ring B is a benzene ring fused to a heterocyclic ring a slight variation is necessary and is described in Scheme 8. 2-Amino-3-nitophenol is treated as described in Scheme 3 to afford the ether 18. This material is heated with an amine of Formula (III) as described in Scheme 7 to provide the compound of Formula (Id). Reduction of the nitro group using sodium dithionite followed by either: 1) treatment with sodium nitrite in acetic acid (according to the procedure of Fries et al., Justus Liebigs Ann. Chem., 511, (1934) 213–230), or 2) heating with a carboxylic acid (according to the procedure of Bugaut and Kalopisses, Ger. Patent DE1921911 700226) to afford compounds of Formula (Ie).

Intermediates of Formulas (II) and (III) are coupled by heating them neat or as a solution in a polar solvent such as methanol, tetrahydrofuran, or dimethylsulfoxide for 6 to 72 hours at temperatures from 25 to 125° C. This provides compounds of Formula (I) or a protected form of compounds of Formula (I). The reaction is conveniently carried out by heating Intermediates (II) and (III) in a mixture of

SCHEME 8

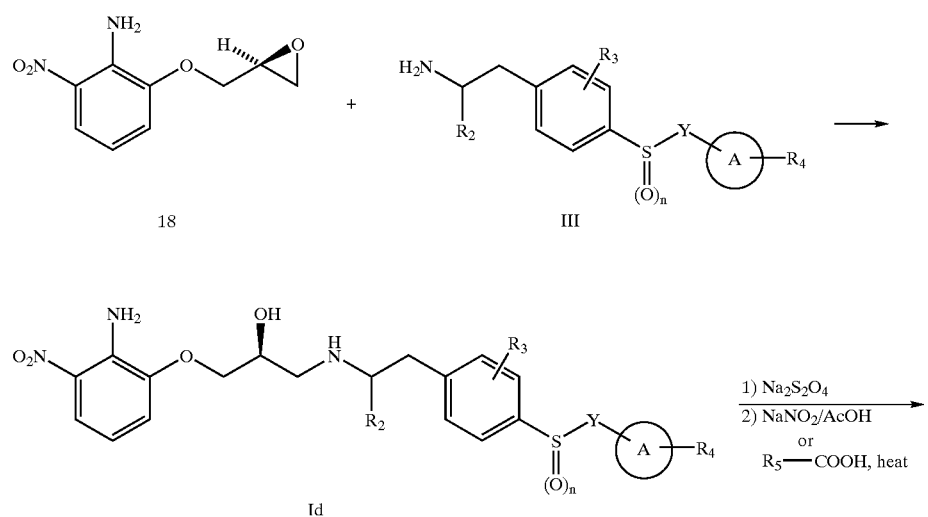

-continued

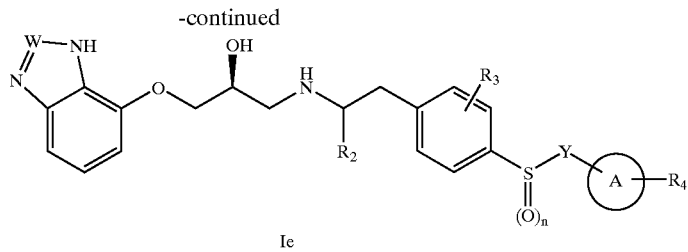

Ie wherein:

W is N, or C-R₅

R₅ is as described previously under Formula (I)

Intermediates of Formulas (IIb) and (III) are coupled by heating them neat or as a solution in a polar solvent such as methanol, tetrahydrofuran, or dimethylsulfoxide for 6 to 72 hours at temperatures from 25 to 145 C. This provides a protected form of compounds of Formula (I). The reaction is conveniently carried out by heating Intermediates (II) and (III) in a mixture of THF and methanol in a sealed tube at 50 to 145° C. for 12 to 48 hours. The silyl protecting group is removed from compound of Formula (Ib) by treatment with TBAF to afford final compound of Formula (I). Other protecting groups would be removed by procedures known by those skilled in the art. This procedure is illustrated in Scheme 9.

SCHEME 9

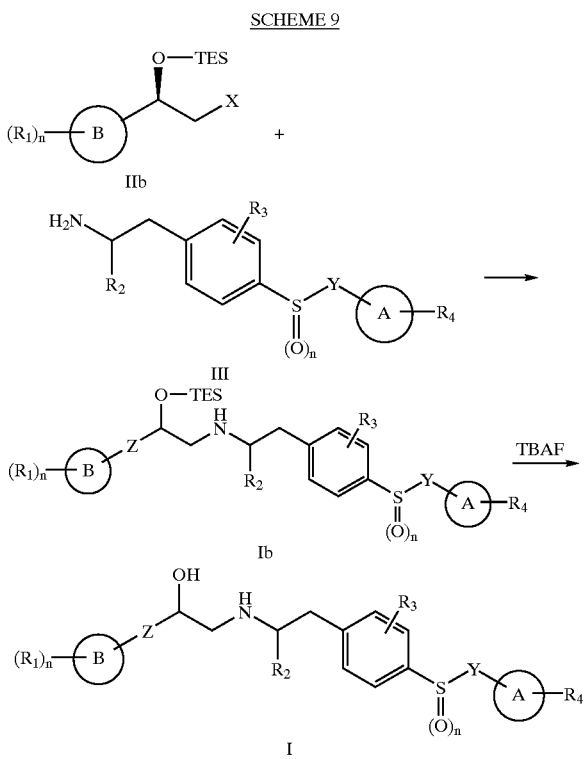

Compounds of the general Formula (I) may be separated into diastereomeric pairs of enantiomers by, for example, fractional crystallization from a suitable solvent such as methanol or acetonitrile or a mixture thereof. The pair of enantiomers thus obtained may be separated into individual optical stereoisomers by conventional means, such as, by the use of an enantiomerically pure chiral organic acid as a resolving agent. Alternatively, any enantiomer of a compound of Formula (I) may be obtained by stereospecific synthesis using optically pure starting materials of known configuration for the preparation of intermediates.

The compounds of this invention are useful in treating metabolic disorders related to insulin resistance or hyperglycemia, typically associated with obesity or glucose intolerance. The compounds of this invention are therefore, particularly useful in the treatment or inhibition of type II diabetes. The compounds of this invention are also useful in modulating glucose levels in disorders such as type I diabetes.

The ability of compounds of this invention to treat or inhibit disorders related to insulin resistance or hyperglycemia was established with representative compounds of this invention in the following standard pharmacological test procedures, which measured the binding selectivity to the $\beta_1$, $\beta_2$, and $\beta_3$ adrenergic receptors. Binding to the receptors was measured in Chinese Hamster ovary (CHO) cells that were transfected with adrenergic receptors. The following briefly summarizes the procedures used and results obtained.

Transfection of CHO cells with $\beta_1$ and $\beta_2$ adrenergic receptors: CHO cells were transfected with human $\beta_1$ or $\beta_2$-adrenergic receptors as described in Tate, K. M., *Eur. J. Biochem.*, 196:357–361 (1991).

Cloning of Human $\beta_3$-AR Genomic DNA: cDNA was constructed by ligating four polymerase chain reaction (PCR) products using the following primers: an ATG-NarI fragment, sense primer 5'-CTTCCCTACCGCCCCACGCGCGATC3' and anti-sense primer 5'CTGGCGCCCAACGGCCAGTGGC-CAGTC3'; a NarI-AccI fragment, 5'TTGGCGCTGATGGC-CACTGGCCGTTTG3' as sense and 5'GCGCGTAGACGAAGAGCATCACGAG3' as anti-sense primer; an AccI-StyI fragment, sense primer 5'CTCGTGAT-GCTCTTCGTCTCACGCGC3' and anti-sense primer 5'GTGAAGGTGCCCATGATGAGACCCAAGG3' and a StyI-TAG fragment, with sense primer 5'CCCTGTGCAC-CTTGGGTCTCATCATGG3' and anti-sense primer 5'CCTCTGCCCCGGTTACCTACCC3'. The corresponding primer sequences are described in Mantzoros, C. S., et. al., *Diabetes* 45: 909–914 (1996). The four fragments are ligated into a pUC 18 plasmid (Gibco-BRL) and sequenced. Full length $\beta_3$ AR clones (402 amino acids) containing the last 6 amino acids of h$\beta_3$ AR are prepared with the $\beta_3$-$\beta$ARpcDNA3 from ATTC.

Binding Procedure: Clones expressing receptor levels of 70 to 110 fmoles/mg protein were used in the test procedures. CHO cells were grown in 24-well tissue culture plates in Dulbecco's Modified Eagle Media with 10% fetal bovine serum, MEM non-essential amino acids, Penicillin-Streptompycin and Geneticin. On the day of test procedure, growth medium was replaced with preincubation media (Dulbecco's Modified Eagle Media and incubated for 30 minutes at 37° C. Preincubation medium was replaced with 0.2 ml treatment medium containing DMEM media containing 250 μM IBMX (isobutyl-1-methylxantine) plus 1 mM ascorbic acid with test compound dissolved in DMSO.

Test compounds were tested over a concentration range of $10^{-9}$M to $10^{-5}$M for $\beta_3$ cells and $10^{-8}$ to $10^{-4}$M for $\beta_1$ and $\beta_2$ transfected cells. Isoproterenol ($10^{-5}$M) was used as an internal standard for comparison of activity. Cells were incubated at 37° C. on a rocker for 30 min with the $\beta_3$ cells and 15 min for $\beta_1$ and $\beta_2$ cells. Incubation was stopped with the addition of 0.2N HCl and neutralized with 2.5N NaOH. The plates, containing the cells and neutralized media, were stored at −20 degrees celsius until ready to test for cAMP using the SPA test kit (Amersham).

Data Analysis and Results: Data collected from the SPA test procedure were analyzed as per cent of the maximal isoproterenol response at $10^{-5}$M. Activity curves were plotted using the SAS statistical and graphics software. $EC_{50}$ values were generated for each compound and the maximal response (IA) developed for each compound is compared to the maximal response of isoproternol at $10^{-5}$M from the following formula:

$$IA = \% \text{ activity compound}/\% \text{ activity isoproterenol}$$

Table I shows the β3-adronergic receptor $EC_{50}$ and IA values for the representative compounds of this invention that were evaluated in this standard pharmacological test procedure. These results show that compounds of the present invention have activity at the β3-adrenergic receptor. The compounds of this invention had weaker or no activity at β1 and/or β2-adrenergic receptor.

TABLE I

| Compound No. | $EC_{50}(\beta 3, \mu M)$ | IA(β3) |
|---|---|---|
| Example 12 | 0.07 | 0.76 |
|  | 0.035 | 0.61 |
| Example 15 | 0.028 | 0.92 |
| Example 19 | 0.068 | 0.95 |
| Example 24 | 0.431 | 0.62 |
| Example 27 | 0.025 | 1 |
| Example 29 | 0.033 | 1.1 |
| Example 32 | 0.33 | 1.2 |
| Example 33 | 0.789 | 0.44 |

Based on the results obtained in these standard pharmacological test procedures, representative compounds of this invention have been shown to be selective $\beta_3$ adrenergic receptor agonists and are therefore useful in treating metabolic disorders related to insulin resistance or hyperglycemia (typically associated with obesity or glucose intolerance), atherosclerosis, gastrointestinal disorders, neurogenetic inflammation, glaucoma, ocular hypertension, and frequent urination; and are particularly useful in the treatment or inhibition of type II diabetes, and in modulating glucose levels in disorders such as type I diabetes. As used herein, the term modulating means maintaining glucose levels within clinically normal ranges.

As used in accordance with this invention, the term providing an effective amount means either directly administering such a compound of this invention, or administering a prodrug, derivative, or analog which will form an effective amount of the compound of this invention within the body.

It is understood that the effective dosage of the active compounds of this invention may vary depending upon the particular compound utilized, the mode of administration, the condition, and severity thereof, of the condition being treated, as well as the various physical factors related to the individual being treated. As used in accordance with invention, satisfactory results may be obtained when the compounds of this invention are administered to the individual in need at a daily dosage of from about 0.1 mg to about 1 mg per kilogram of body weight, preferably administered in divided doses two to six times per day, or in a sustained release form. For most large mammals, the total daily dosage is from about 3.5 mg to about 140 mg. It is preferred that the administration of one or more of the compounds herein begin at a low dose and be increased until the desired effects are achieved.

Such doses may be administered in any manner useful in directing the active compounds herein to the recipient's bloodstream, including orally, via implants, parenterally (including intravenous, intraperitoneal and subcutaneous injections), rectally, intranasally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s).

In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

The compounds of the present invention also possess utility for increasing lean meat deposition and/or improving lean meat to fat ratio in edible animals, i.e. ungulate animals and poultry.

Animal feed compositions effective for increasing lean meat deposition and for improving lean meat to fat ratio in poultry, swine, sheep, goats, and cattle are generally prepared by mixing the compounds of the present invention with a sufficient amount of animal feed to provide from about 1 to 1000 ppm of the compound in the feed. Animal feed supplements can be prepared by admixing about 75% to 95% by weight of a compound of the present invention with about 5% to about 25% by weight of a suitable carrier or diluent. Carriers suitable for use to make up the feed supplement compositions include the following: alfalfa meal, soybean meal, cottonseed oil meal, linseed oil meal, sodium chloride, cornmeal, cane molasses, urea, bone meal, corncob meal and the like. The carrier promotes a uniform distribution of the active ingredients in the finished feed into which the supplement is blended. It thus performs an important function by ensuring proper distribution of the active ingredient throughout the feed. The supplement is used as a top dressing for the feed, it likewise helps to ensure uniformity of distribution of the active material across the top of the dressed feed.

The preferred medicated swine, cattle, sheep and goat feed generally contain from 0.01 to 400 grams of active ingredient per ton of feed, the optimum amount for these animals usually being about 50 to 300 grams per ton of feed. The preferred poultry and domestic pet feed usually contain about 0.01 to 400 grams and preferably 10 to 400 grams of active ingredient per ton of feed.

For parenteral administration the compounds of the present invention may be prepared in the form of a paste or a pellet and administered as an implant, usually under the skin of the head or ear of the animal in which increase in lean meat deposition and improvement in lean mean to fat ratio is sought. In general, parenteral administration involves injection of a sufficient amount of the compounds of the present invention to provide the animal with 0.001 to 100 mg/kg/day of body weight of the active ingredient. The preferred dosage for swine, cattle, sheep and goats is in the range of from 0.001 to 50 mg/kg/day of body weight of active ingredient; whereas, the preferred dose level for poultry and domestic pets is usually in the range of from 0.001 to 35 mg/kg/day of body weight.

Paste formulations can be prepared by dispersing the active compounds in a pharmaceutically acceptable oil such as peanut oil, sesame oil, corn oil or the like. Pellets containing an effective amount of the compounds of the present invention can be prepared by admixing the compounds of the present invention with a diluent such as carbowax, carnuba wax, and the like, and a lubricant, such as magnesium or calcium stearate, can be added to improve the pelleting process. It is, of course, recognized that more than one pellet may be administered to an animal to achieve the desired dose level which will provide the increase in lean meat deposition and improvement in lean meat to fat ratio desired. Moreover, it has been found that implants may also be made periodically during the animal treatment period in order to maintain the proper drug level in the animal's body.

For the poultry and swine raisers, using the method of the present invention yields leaner animals.

Additionally, the compounds of this invention are useful in increasing the lean mass to fat ratio in domestic pets, for the pet owner or veterinarian who wishes to increase leanness and trim unwanted fat from pet animals, the present invention provides the means by which this can be accomplished.

The following procedures describe the preparation of representative examples of this invention.

EXAMPLE 1

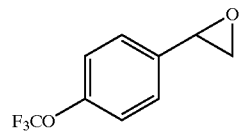

(4-Trifluoromethoxyphenyl)oxirane

To a suspension of sodium hydride(1.54 g, 38.46 mmol) in 35 mL of dry DMSO was added, via a solid addition funnel, trimethylsulfoxonium iodide (7.84 g, 35.61 mmol) over 5 minutes. After $H_2$ gas evolution ceases the cloudy solution was treated with a solution of 4-trifluoromethoxybenzaldehyde (4.96 g, 25.05 mmol) in 35 mL of THF over 15 minutes. After one hour, 1 mL of ethanol was slowly added, then the THF and ethanol were removed by rotary evaporation. The DMSO solution was poured into 100 mL of water and then extracted with dichloromethane (3×75 mL). The combined organic extracts were washed with dilute brine (2×75 mL), dried ($Na_2SO_4$), filtered, evaporated and purified by flash chromatography (silica gel, 10% ethyl acetate/hexane). This procedure afforded 1.95 g of the title compound as a colorless oil.

$^1$H NMR (300 MHz, $CDCl_3$) δ7.33–7.17 (series of m, 4H), 3.86 (m, 1H), 3.14 (m, 1H) and 2.76 (m, 1H).

EXAMPLE 2

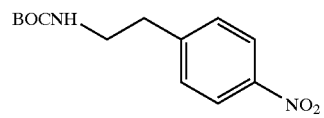

tert-butyl 4-nitrophenethylcarbamate

To a cold suspension of 4-nitrophenethylamine hydrochloride (20.0 g, 98.7 mmol) in chloroform (200 mL) was added triethylamine (9.99 g, 98.7 mmol). This solution was treated with di-t-butyldicarbonate (23.70 g, 108.6 mmol) portionwise. After 15 minutes the ice/water bath was removed and the reaction was stirred at room temperature overnight. The reaction mixture was successively washed with the following: water (1×), 0.5M hydrochloric acid (2×), dilute aqueous sodium bicarbonate (1×), brine (1×). The organic phase was dried ($Na_2SO_4$), filtered, evaporated, and flash chromatographed (silica gel, 33% ethyl acetate/hexane) to afford 24.2 g of the title compound as a light yellow solid.

$^1$H NMR (300 MHz, $CDCl_3$) δ8.05 (d, J=8.2 Hz, 2H), 7.42 (d, J=8.2 Hz, 2H), 3.06 (q, J=7.1 Hz, 2H), 2.58 (t, J=7.1 Hz, 2H) and 1.29 (s, 9H).

EXAMPLE 3

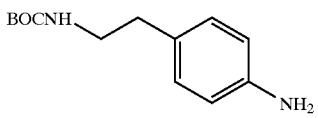

tert-butyl 4-aminophenethylcarbamate

To a solution of N-(tert-butoxycarbonyl)-4-nitrophenethyl-2-amine from Example 2 (24.2 g, 96.7 mmol) in a mixture of ethanol (150 mL) and THF (50 mL) was added 5% Pd/C (4.0 g). This solution was placed on a Parr Hydrogenator under 40 psig of hydrogen gas and shaken for 5 hours. The reaction mixture was filtered and evaporated to leave a colorless oil. This oil was taken up into hot hexane/ethyl acetate and allowed to crystallized overnight. The solid was collected via vacuum filtration and placed under high vacuum for eight hours. 19.31 g of the title compound, as a white solid, was obtained.

$^1$H NMR (300 MHz, DMSO-$d_6$) δ6.81 (d, J=8.1 HZ, 2H), 6.46 (d, J=8.1 Hz, 2H), 4.82 (s, 2H(exch.)), 3.01 (q, J=7.2 Hz, 2H), 2.48 (t, J=7.2 Hz, 2H) and 1.36 (s, 9H).

EXAMPLE 4

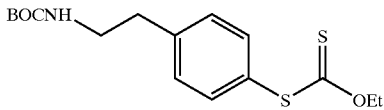

S-(4-{2-[( tert-butoxycarbonyl)amino]ethyl}phenyl) O-methyl carbonodithioate

The aniline from Example 3 (6.91 g, 29.24 mmol) was stirred into cold dilute hydrochloric acid (made from 50 mL of water and 6 mL of concentrated hydrochloric acid) and treated with a solution of sodium nitrite (3.00 g, 43.48 mmol) in water (14 mL) portionwise over 20 minutes. After addition was complete vigorous stirring was continued for 5 minutes. To this cold solution was added nickel(II)chloride hexahydrate (5–10 mg).

During the sodium nitrite additions, a solution of potassium ethyl xanthate (10.26 g, 64.0 mmol) in dilute aqueous sodium bicarbonate (made from 65 mL of water and 6.5 g of sodium bicarbonate) was prepared and warmed to 75° C.

The cold diazonium solution above was added portionwise (2.5 mL every 30 seconds) to the well stirred warm xanthate solution. A yellow oil formed upon the evolution of gas bubbles. The mixture was stirred and heated for an additional 10 minutes after additions were complete. The solution was then cooled to 5° C., and the aqueous solvent decanted from the yellow oil. The oily residue was taken up into dichloromethane, dried(Na$_2$SO$_4$), filtered and evaporated. The title compound was purified by flash chromatography (silica gel, 33% diethyl ether/hexane) to afford 3.75 g of a yellow oil that solidified upon standing.

$^1$H NMR (300 MHz, CDCl$_3$) δ7.44 (d, J=8.2 Hz, 2H), 7.26 (d, J=8.2 Hz, 2H) 4.62 (q, J=7.2 Hz, 2H), 3.40 (m, 2H), 2.85 (t, J=7.0 Hz, 2H), 1.44 (s, 9H) and 1.34 (t, J=7.0 Hz, 3H).

EXAMPLE 5

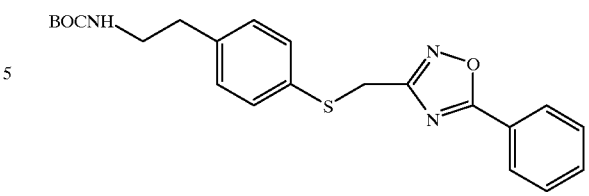

tert-butyl 4-{[(5-phenyl-1,2,4-oxadiazol-3-yl) methyl]sulfanyl}phenethylcarbamate To a room temperature degassed solution of the xanthate from example 4 (2.44 g, 7.15 mmol) in dry ethanol (35 mL) was added freshly powdered sodium borohydride (0.622 g, 16.43 mmol). 30 minutes after addition the solution was warmed to 45° C. for 1 h. The reaction mixture was recooled to room temperature and 3-chloromethyl-5-phenyl-1,2,4-oxadiazole (1.39 g, 7.145 mmol) was added. The reaction was warmed to 50° C. for 3 h. The reaction was quenched with dilute hydrochloric acid and the pH adjusted to 7.5 with aqueous sodium bicarbonate. The ethanol was removed by evaporation in vacuo and the residue was extracted with dichloromethane, The organic solution was dried (Na$_2$SO$_4$), filtered, and evaporated. The title compound was purified by flash chromatography (silica gel, 33% diethyl ether/hexane) to afford 2.45 g of a white solid.

$^1$H NMR (300 MHz, CDCl$_3$) δ8.17 (m, 2H), 7.65–7.50 (m, 3H), 7.40 (d, J=8.1 Hz, 2H), 7.13 (d, J=8.1 Hz, 2H), 4.19 (s, 2H), 3.35 (br m, 2H), 2.76 (t, J=6.9 Hz, 2H) and 1.43 (s, 9H).

EXAMPLE 6

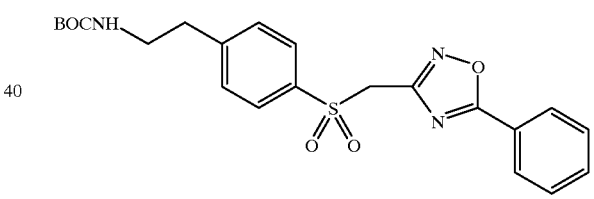

tert-butyl 4-{[(5-phenyl-1,2,4-oxadiazol-3-yl) methyl]sulfonyl}phenethylcarbamate To a solution of the sulfide of Example 5 (2.40 g, 5.83 mmol) in dichloromethane (24 mL) at 0° C. was added purified mCPBA (2.21 g, 12.83 mmol) in dichloromethane (14 mL). After 1 h the ice/water bath was remove and the reaction was run for 1 h more. TLC shows no starting material and one slower running product spot. Additional dichloromethane was added and the mixture was washed with dilute aqueous sodium dithionite (1×) followed by 50% aqueous sodium bicarbonate (2×). The organic phase was dried (Na$_2$SO$_4$), filtered and evaporated. The residue was taken up into a solution of dichloromethane and diethyl ether and passed through a 5 cm pad of silica gel. Thorough removal of solvent in vacuo afforded 2.55 g of the title compound as a white solid.

$^1$H NMR (300 MHz, CDCl$_3$) δ8.15 (m, 2H), 7.82 (d, J=8.5 Hz, 2H), 7.64–7.53 (m, 3H), 7.38 (d, J=8.5 Hz, 2H), 4.60 (s, 2H), 3.40 (br m, 2H), 2.91 (t, J=7.0 Hz, 2H) and 1.44 (s, 9H).

EXAMPLE 7

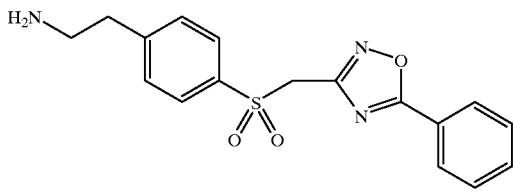

4{[(5-phenyl-1 2,4-oxadiazol-3-yl)methyl]sulfonyl}phenethylamine

To a solution of the sulfone of Example 6 (2.40 g, 5.41 mmol) in dichloromethane (32 mL) and methanol (5 drops) was added trifluoroacetic acid (8 mL). This mixture was stirred for 4 h, and TLC indicated the absence of starting material. The volatile components were removed in vacuo and the residue was taken up into dichloromethane (50 mL) and washed with dilute aqueous sodium bicarbonate (2×). The organic phase was dried ($Na_2SO_4$), filtered and completely evaporated to leave 1.76 g of pure title compound.

$^1$H NMR (300 MHz, DMSO-$d_6$) δ8.13 (m, 2H), 7.84 (d, J=8.4 Hz, 2H), 7.62–7.55 (m, 3H), 7.54 (d, J=8.4 Hz, 2H), 4.95 (s, 2H), 3.10 (m, 2H) and 2.97 (m, 2H). MS (ESI(+)), [M+H]$^+$ @ m/z 344.

EXAMPLE 8

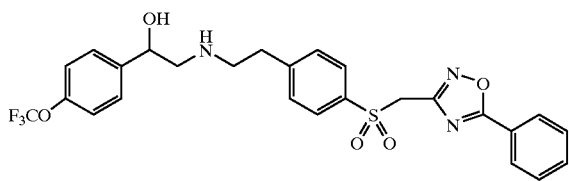

2-[(4{[(5-phenyl-1,2,4-oxadiazol-3-yl)methyl]sulfonyl}phenethyl)amino]-1-[4-(trifluoromethoxy)phenyl]-1-ethanol A solution of (4-trifluoromethoxyphenyl)oxirane (0.278 g, 1.36 mmol) and the amine of Example 7 (0.779 g, 2.27 mmol) in methanol (7.5 mL) was heated to 45° C. for 22 h. TLC shows characteristic product spot at $R_f$=0.2 (silica gel plate; dichloromethane/chloroform/methanol: 10/3/2). The reaction mixture was cooled, silica gel (5 g) was added and the methanol was remove in vacuo. The reaction mixture, preabsorbed onto silica gel, was applied to the top of a flash chromatography column and purified in the standard manner. The white foam obtained was crystallized from hot diethyl ether to afford 0.091 g of the title compound as a white crystalline solid. MP=125–127° C.

$^1$H NMR (400 MHz, DMSO-$d_6$) δ8.01–7.27 (series of m, 13H), 5.40 (br, 1 H), 5.08 (s, 2H), 4.64 (br s, 1H), 2.80 (s, 4H) and 2.66 (m, 2H).

MS(ESI(+)), [M+H]$^+$ @ 548

Anal: calcd; C., 57.03; H, 4.42; N, 7.67 found; C., 56.78; H, 4.45; N, 7.52

EXAMPLE 9

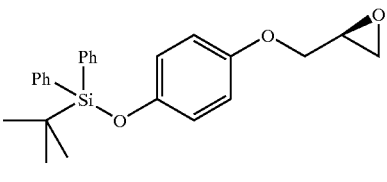

tert-butyl{4-[(2S)oxiranylmethoxy]phenoxy}diphenylsilane

To a cold solution of 4-(diphenyl-tert-butylsilyloxy)phenol (19.60 g, 56.24 mmol), R-(+)-glycidol (6.16 mL, 92.80 mmol), and triphenylphosphine (24.34 g, 92.80 mmol) in benzene (140 mL) and THF (20 mL) was added DEAD (15.06 mL, 95.60 mmol) in benzene (20 mL) dropwise. After addition of the DEAD the ice/water bath was removed and the reaction mixture was allowed to stir at room temperature for 18 h. Ethyl acetate (75 mL) was added to the purple solution and it was filtered through a 5 cm pad of silica gel. The filtrate was evaporated in vacuo and a solution of hexane (100 mL) and ether (100 mL) was added to precipitate the triphenylphosphine oxide; this was removed by vacuum filtration. Silica gel (150 g) was added to the filtrate and the solvent was removed in vacuo. The reaction mixture, preabsorbed onto silica gel was applied to the top of a flash chromatography column and purified in the standard manner (silica gel, 33% diethyl ether/hexane as eluant). This procedure afforded 13.53 g of the title compound as a white solid.

$^1$H NMR (400 MHz, CDCl$_3$) δ7.71 (m, 4H), 7.37 (m, 6H), 6.66 (ABq, J=5.1 Hz, 4H) 4.07 (AXm, 1H), 3.84 (AXm, 1H), 3.28 (m, 1H), 2.86 (AXt, J=4.3 Hz, 1H), 2.70 (AXm, 1H) and 1.09 (s, 9H).

EXAMPLE 10

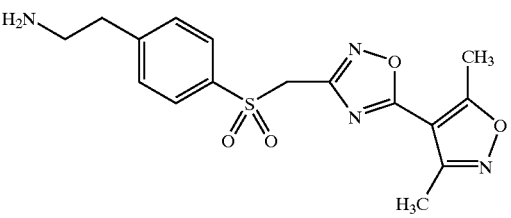

4-({[5-(3,5-dimethyl-4-isoxazolyl)-1,2,4-oxadiazol-3-yl]methyl}sulfonyl)phenethylamine Following the procedures described in Examples 5, 6, and 7 using 3-(chloromethyl)-5-(3,5,-dimethylisoxazol-4-yl)-1,2,4-oxadiazole as alkylating agent afforded the title compound.

$^1$H NMR (300 MHz, CDCl$_3$) δ7.84 (d, J=8.2 Hz, 2H), 7.40 (d, J=8.2 Hz, 2H), 4.60 (s, 2H), 3.05 (m, 2H), 2.92 (t, J=7.2 Hz, 2H), 2.73 (s, 3H) and 2.49 (s, 3H).

EXAMPLE 11

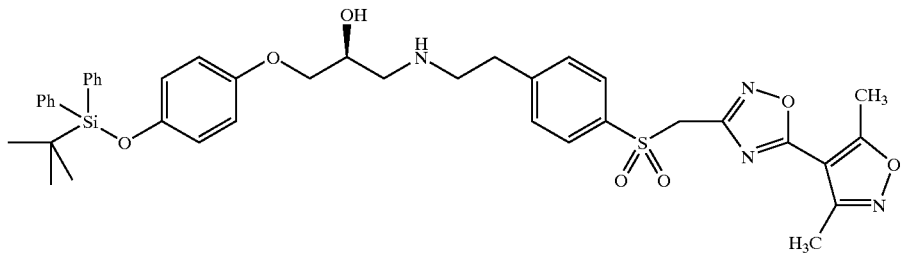

(2S)-1-(4-{[tert-butyl(diphenyl)sily]oxy}phenoxy)-3-{[4-({[5-(3,5-dimethyl-4-isoxazolyl)-1,2,4,-oxadiazol-3-yl]methyl}sulfonyl)phenethyl]amino}-2-propanol A solution of the amine of Example 10 (0.410 g, 1.13 mmol) and the epoxide of Example 9 (0.4046 g, 1.00 mmol) in a mixture of methanol (12 mL) and THF (3 mL) was heated to 45° C. for 23 h. TLC shows characteristic product spot at $R_f$=0.2 5(silica gel plate; dichloromethane/chloroform/methanol: 20/5/2). The reaction mixture was cooled, silica gel (5 g) was added and the methanol was remove in vacuo. The reaction mixture, preabsorbed onto silica gel was applied to the top of a flash chromatography column (silica gel; dichloromethane/chloroform/methanol: 12/3/1) and purified in the standard manner. This procedure afforded 0.410 g of the title compound as a white foam.

$^1$H NMR (300 MHz, CDCl$_3$) δ7.82 (d, J=8.3 Hz, 2H), 7.70 (m, 4H), 7.38 (m, 8H), 6.65 (ABq, J=9.1 Hz, 4H), 4.58 (s, 2H), 4.00 (m, 1H), 3.84 (d, J=5.1 Hz, 2H), 3.00–2.74 (series of m, 6H), 2.72 (s, 3H), 2.48 (s, 3H) and 1.08 (s, 9H).

EXAMPLE 12

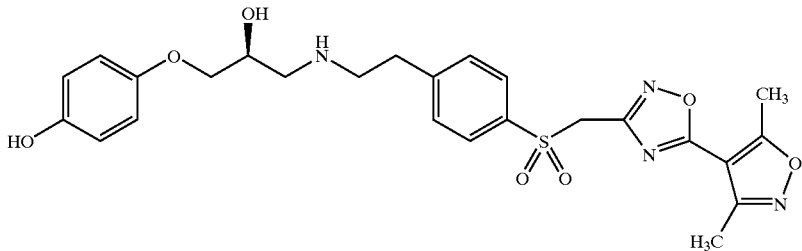

4-[((2S)-3-{[4-({[5-(3,5-dimethyl-4-isoxazolyl)-1,2,4-oxadiazol-3-yl]methyl}sulfonyl)phenethyl]amino}-2-hydroxypropyl)oxy]phenol To a solution of the amino alcohol of Example 11(0.40 g, 0.52 mmol) in THF (9 mL) was added a 1M solution of TBAF (0.13 mL, 0.13 mmol). The reaction mixture was stirred for 6 h. TLC shows the absence of starting material, so 3 drops of a saturated aqueous ammonium chloride solution was added. The reaction mixture was evaporated in vacuo to dryness and the residue was flash chromatographed (silica gel; dichloromethane/chloroform/methanol: 12/3/1) to afford 0.120 g of the title compound as a white foam.

$^1$H NMR (400 MHz, DMSO-d$_6$) δ8.85 (s, 1H), 7.77 (d, J=8.1 Hz, 2H), 7.48 (d, J=8.1 Hz 2H), 6.67 (ABq, J=6.8 Hz, 4H), 5.09 (s, 2H), 4.90 (br s, 1H), 3.82–3.70 (m, 3H), 2.81 (br s, 4H), 2.74–2.65 (m, 1H), 2.62 (m, 3H), 2.61–2.55 (m, 1H) and 2.34 (s, 3H).

MS(ESI(+)), [M+H]$^+$ @ m/z 529.

Anal: calcd (as monohydrate); C, 54.93; H, 5.54; N, 10.25 found; C, 54.57; H, 5.10; N, 9.93.

EXAMPLE 13

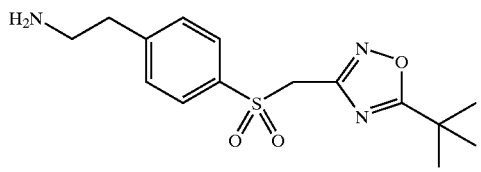

4-({[5-(tert-butyl)-1,2,4-oxadiazol-3-yl]methyl}sulfonyl)phenethylamine

Following the procedures described in Examples 5, 6, and 7 using 3-(chloromethyl)-5-tert-butyl-1,2,4-oxadiazole as alkylating agent afforded the title compound.

$^1$H NMR (300 MHz, CDCl$_3$) δ7.78 (d, J=8.2 Hz, 2H), 7.37 (d, J=8.2 Hz, 2H), 4.52 (s, 2H), 3.00 (m, 2H), 2.90 (t, J=7.0 Hz, 2H) and 1.38 (s, 9H).

MS(ESI(+)), [M+H]$^+$ @ m/z 324.

EXAMPLE 14

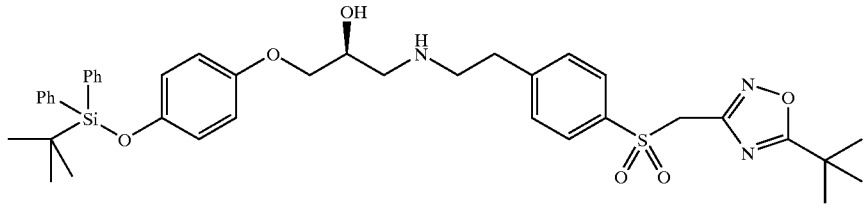

(2S)-1-(4-{[tert-butyl(diphenyl)silyl]oxy}phenoxy)-3-{[4-({[5-(tert-butyl)-1,2,4-oxadiazol-3-yl]methyl}sulfonyl)phenethyl]amino}-2-propanol A solution of the amine of Example 13 (0.873 g, 2.70 mmol) and tert-butyl{4-[(2S)oxiranylmethoxy]phenoxy}diphenylsilane (0.980 g, 2.42 mmol) in a mixture of methanol (20 mL) and THF (3 mL) was heated to 45° C. for 23 h. TLC shows characteristic product spot at $R_f$=0.25 (silica gel plate; dichloromethane/chloroform/methanol: 20/5/2). The reaction mixture was cooled, silica gel (5 g) was added and the methanol was remove in vacuo. The reaction mixture, preabsorbed onto silica gel was applied to the top of a flash chromatography column (silica gel; dichloromethane/chloroform/methanol: 12/3/1) and purified in the standard manner. This procedure afforded 0.660 g of the title compound as a white foam.

$^1$H NMR (300 MHz, CDCl$_3$) δ7.78–7.66 (m, 6H), 7.45–7.32 (m, 8H), 6.64 (ABQ, J=7.8 Hz, 4H), 4.50 (s, 2H), 4.00 (m, 1H), 3.84 (d, J=5.0 Hz, 2H), 2.95–2.70 (m, 6H,) 1.37 (s, 9H) and 1.08 (s, 9H).

MS(ESI(+)), [M+H]$^+$ 729.

EXAMPLE 15

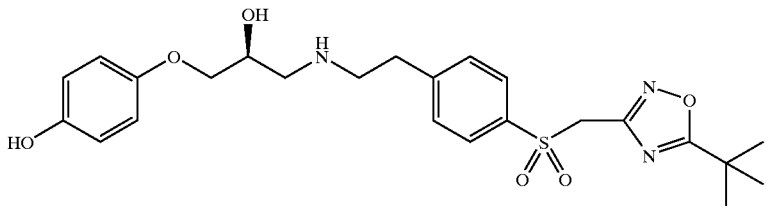

4-[((2S)-3-{[4-({[5-(tert-butyl)-1,2,4-oxadiazol-3-yl]methyl}sulfonyl)phenethyl]amino}-2-hydroxypropyl)oxy]phenol To a solution of the amino alcohol of Example 14(0.650 g, 0.90 mmol) in THF (12 mL) was added a 1 M solution of TBAF (0.225 mL, 0.225 mmol). The reaction mixture was stirred for 6 h. TLC showed the absence of starting material, therefore 5 drops of a saturated aqueous ammonium chloride solution was added. The reaction mixture was evaporated in vacuo to dryness and the residue was flash chromatographed (silica gel; dichloromethane/chloroform/methanol: 15/5/3) to afford 0.280 g of the title compound as a white foam.

$^1$H NMR (400 MHz, DMSO-d$_6$) δ8.87 (s, 1H), 7.67 (d, J=8.1 Hz, 2H), 7.45 (d, J=8.1 Hz, 2H), 6.71 (d, J=9.0 Hz, 2H), 6.64 (d, J=9.0 Hz, 2H), 4.94 (s, 2H), 4.92 (br, 1H), 3.79–3.72 (m, 2H), 2.80 (s, 4H), 2.68 (m, 1H), 2.58 (m, 1H) and 1.27 (s, 9H).

MS(ESI(+)), [M+H]+ @ m/z 490.

Anal: calcd; C., 58.88; H, 6.38; N, 8.58 found; C., 58.98; H, 6.55; N, 8.12.

EXAMPLE 16

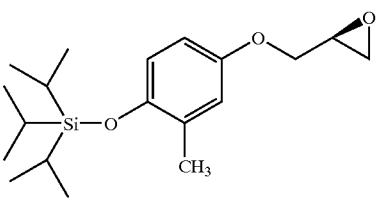

Triisopropyl{2-methyl-4-](2S)oxiranylmethoxy]phenoxy}silane

To a cold solution of 4-(triisopropylsilyloxy)-3-methylphenol (7.73 g, 27.56 mmol), R-(+)-glycidol (4.02 mL, 60.63 mmol), and triphenylphosphine (15.90 g, 60.63 mmol) in benzene (50 mL) and THF (50 mL) was added DEAD (9.76 mL, 62.01 mmol) in benzene (12 mL) dropwise. After addition of the DEAD the ice/water bath was removed and the reaction mixture was allowed to stir at room temperature for 18 h. The reaction was warmed to 55° C. for 4 h then cooled to room temperature. Ethyl acetate (40 mL) was added to the purple solution and it was filtered through a 5 cm pad of silica gel. The filtrate was evaporated in vacuo and a solution of hexane (70 mL) and ether (70 mL) was added to precipitate the triphenylphosphine oxide, this was removed by vacuum filtration. Silica gel (90 g) was added to the filtrate and the solvent was removed in vacuo. The reaction mixture, preabsorbed onto silica gel was applied to the top of a flash chromatography column and purified in the standard manner (silica gel, 20% diethyl ether /hexane as eluant). This procedure afforded 5.83 g of the title compound as a white solid.

$^1$H NMR (300 MHz, CDCl$_3$) δ6.67 (m, 2H), 6.58 (dd, J=8.2 and 3.1 Hz, 1H), 4.12 (AXm, 1H), 3.90 (AXm, 1H), 3.32 (m, 1H), 2.88 (AXt, J=5.0 Hz, 1H), 2.74 (AXm, 1H), 2.21 (s, 3H), 1.27 (m, 3H) and 1.10 (m, 18H).

EXAMPLE 17

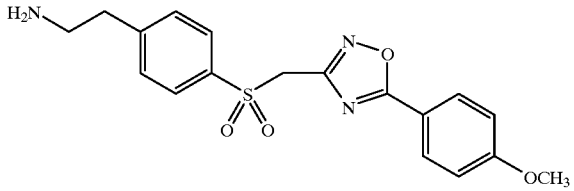

4-({[5-(4-methoxyphenyl)-1,2,4-oxadiazol-3-yl]methyl}sulfonyl)phenethylamine

Following the procedures described in Examples 5, 6, and 7 using 3-chloromethyl-5-(4-methoxyphenyl)-1,2,4-oxadiazole as alkylating agent afforded the title compound.

$^1$H NMR (300 MHz, DMSO-d$_6$) δ7.96 (d, J=8.9 Hz, 2H), 7.84 (d, J=8.3 Hz, 2H), 7.84 (d, J=8.3 Hz 2H), 7.54 (d, J=8.9 Hz, 2H), 7.16 (d, J=8.3 Hz, 2H), 5.07(s, 2H), 3.86 (s, 3H), 3.32 (br s, 2H), 3.09 (m, 2H) and 2.97 (m, 2H).

MS(ESI(+)), [M+H]$^+$ @ m/z 374.

EXAMPLE 18

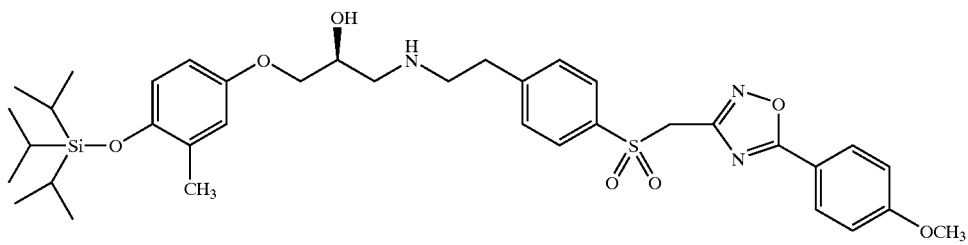

(2S)-1-{[4-({[5-(4-methoxyphenyl)-1,2,4-oxadiazol-3yl]methyl}sulfonyl)phenethyl]amino}-3-{-3-methyl-4[(triisopropylsilyl)oxy]phenoxy}-2-propanol A solution of oxirane of Example 16 (0.430 g, 1.285 mmol) and the amine of Example 17 (0.800 g, 2.142 mmol) in methanol (15 mL) was heated to 45° C. for 44 h. TLC shows characteristic product spot at R$_f$=0.3 (silica gel plate; chloroform/methanol: 10/1). The reaction mixture was cooled, and the methanol was remove in vacuo. The residue was purified by flash chromatography (silica gel, 5% methanol/chloroform) to afford 0.63 g of the title compound as a white foam.

$^1$H NMR (300 MHz, DMSO-d$_6$) δ7.93 (d, J=8.8 Hz, 2H), 7.74 (d, J=8.1 Hz, 2H), 7.47 (d, J=8.1 Hz, 2H), 7.13 (d, J=8.8 Hz, 2H), 6.60 (m, 2H), 6.50 (m, 1H), 5.02 (s, 2H), 4.90 (br, 1H), 3.85 (s, 3H), 3.77 (m, 3H), 2.80 (br m, 4H), 2.68 (m, 1H), 2.57 (m, 1H), 2.01 (s, 3H), 1.37 (m, 3H) and 1.08 (m, 18H).

EXAMPLE 19

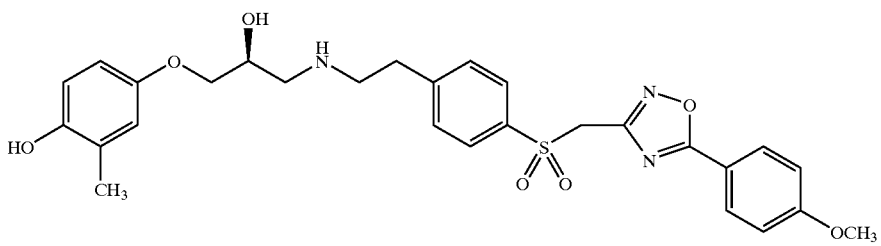

4-[((2S)-2-hydroxy-3-{[4-({[5-(4-methoxyphenyl)-1,2,4-oxadiazol-3-yl]methyl}sulfonyl)phenethyl]amino}propyl)oxy]-2-methylphenol To a solution of the amino alcohol of Example 18(0.630 g, 0.887 mmol) in THF (12 mL) was added a 1M solution of TBAF (0.18 mL, 0.18 mmol). The reaction mixture was stirred for 6 h. TLC shows the absence of starting material, so 4 drops of a saturated aqueous ammonium chloride solution was added. The reaction mixture was evaporated in vacuo to dryness and the residue was flash chromatographed (silica gel; dichloromethane/chloroform/methanol: 5/4/1) to afford 0.357 g of the title compound as a white crystalline solid.

$^1$H NMR (400 MHz, DMSO-d$_6$) δ8.72 (s, 1H), 7.94 (d, J=8.8 Hz, 2H), 7.75 (d, J=8.1 Hz, 2H), 7.48 (d, J=8.1 Hz, 2H), 7.14 (d, J=8.8 Hz, 2H), 6.62 (m, 2H), 6.52 (m, 1H), 5.02 (s, 2H), 4.90 (br 1H), 3.85 (s, 3H), 3.84–3.72 (m, 3H), 2.80 (m, 4H), 2.68 (ABdd, J=11.8 and 4.2 Hx, 1H), 2.57 (ABdd, J=11.8 and 6.6 Hz, 1H) and 2.06 (s, 3H).

MS(APCI(+)), [M+H]$^+$ @ m/z 554.

Anal: calcd (as monohydrate); C., 58.83; H, 5.82; N, 7.35 found; C., 58.80; H, 5.64; N, 7.26.

EXAMPLE 20

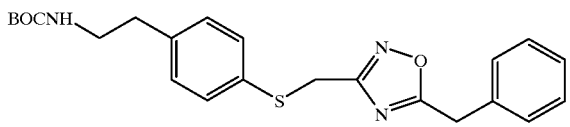

tert-butyl 4-{[(5-benzyl-1,2,4-oxadiazol-3-yl)methyl]sulfanyl}phenethylcarbamate To a room temperature degassed solution of the xanthate from Example 4 (1.96 g, 5.75 mmol) in dry ethanol (30 mL) was added freshly powdered sodium borohydride (0.50 g, 13.23 mmol). 30 minutes after addition the solution was warmed to 45° C. for 1 h. The reaction mixture was recooled to room temperature and 3-chloromethyl-5-benzyl-1,2,4-oxadiazole (1.20 g, 5.75 mmol) was added. The reaction was warmed to 50° C. for 3 h. The reaction was quenched with dilute hydrochloric acid and the pH adjusted to 7.5 with aqueous sodium bicarbonate. The ethanol was removed by evaporation in vacuo and the residue was extracted with dichloromethane, The organic solution was dried ($Na_2SO_4$), filtered, and evaporated. The title compound was purified by flash chromatography (silica gel, 20% ethyl acetate/hexane) to afford 2.34 g of a white solid.

$^1$H NMR (300 MHz, $CDCl_3$) δ7.45–7.05 (series of m, 9H), 4.11 (s, 2H), 3.72 (s, 2H), 3.35 (br m, 2H), 2.76 (m, 2H) and 1.41 (s, 9H).

EXAMPLE 21

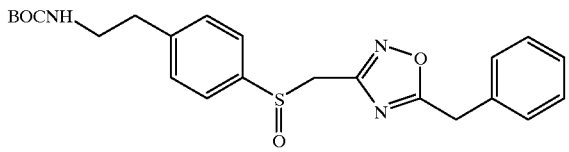

tert-butyl 4-{[(5-benzyl-1,2,4-oxadiazol-3-yl)methyl]sulfinyl}phenethylcarbamate To a solution of the sulfide of Example 20 (1.00 g, 2.35 mmol) in dichloromethane (12 mL) at 0° C. was added purified mCPBA (0.423 g, 2.45 mmol) in dichloromethane (5 mL). After 1 h the ice/water bath was remove and the reaction was run for 1 h more. TLC shows no starting material and one slower running product spot. Additional dichloromethane was added and the mixture was washed with dilute aqueous sodium dithionite (1×) followed by 50% aqueous sodium bicarbonate (2×). The organic phase was dried ($Na_2SO_4$), filtered and evaporated. The residue was taken up into a solution of dichloromethane and diethyl ether and passed through a 5 cm pad of silica gel. Thorough removal of solvent in vacuo afforded 0.928 g of the title compound as a white solid.

$^1$H NMR (300 MHz, $CDCl_3$) δ7.56 (d, J=8.4 Hz, 2H), 7.49–7.25 (series of m, 7H), 4.42–4.15 (series of m, 4H), 3.36 (m, 2H), 2.84 (m, 2H) and 1.41 (s, 9H).

EXAMPLE 22

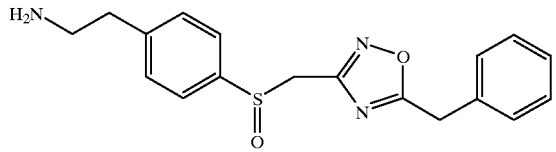

4-{[(5-benzyl-1,2,4-oxadiazol-3-yl)methyl]sulfinyl}phenethylamine

To a solution of the sulfoxide of Example 21 (0.92 g, 2.04 mmol) in dichloromethane (14 mL) and methanol (2 drops) was added trifluoroacetic acid (3.5 mL). This mixture was stirred for 4 h, and TLC indicated the absence of starting material. The volatile components were removed in vacuo and the residue was taken up into dichloromethane (50 mL) and washed with dilute aqueous sodium bicarbonate (2×). The organic phase was dried ($Na_2SO_4$), filtered and completely evaporated to leave 0.71 g of pure title compound.

$^1$H NMR (300 MHz, DMSO-$d_6$) δ7.51 (d, J=8.3 Hz, 2H), 7.43–7.25 (series of m, 7H), 4.39–4.22 (series of m, 4H), 3.31 (br, 2H), 2.92 (m, 2H) and 2.82 (m, 2H).

MS(ESI(+)), [M+H]$^+$ @ m/z 342.

EXAMPLE 23

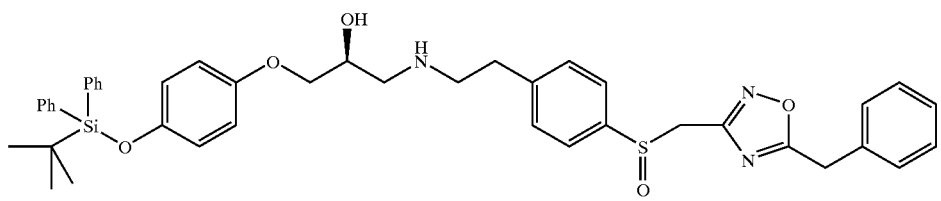

(2S)-1-[(4-{[(5-benzyl-1,2,4-oxadiazol-3-yl)methyl]sulfinyl}phenethyl)amino]-3-(4-{[tert-butyl(diphenyl)silyl]oxy}phenoxy)-2-propanol A solution of the amine of Example 22 (0.705 g, 2.00 mmol) and the epoxide of Example 9 (0.640 g, 1.594 mmol) in a mixture of methanol (25 mL) and THF (5 mL) was heated to 45° C. for 23 h. TLC shows characteristic product spot at $R_f$=0.2 5(silica gel plate; dichloromethane/chloroform/methanol: 20/5/2). The reaction mixture was cooled, silica gel (5 g) was added and the methanol was remove in vacuo. The reaction mixture, preabsorbed onto silica gel was applied to the top of a flash chromatography column(silica gel; dichloromethane/chloroform/methanol: 12/3/1) and purified in the standard manner. This procedure afforded 0.490 g of the title compound as a white foam.

¹H NMR (300 MHz, CDCl₃) δ7.70 (m, 4H), 7.50 (d, J=8.3 Hz, 2H), 7.44–7.20 (series of m, 13H), 6.63 (ABq, J=9.2 and 3.9 Hz, 4H), 4.41–4.21 (series of m, 4H), 3.81–3.68 (m, 3H), 2.78 (br s, 4H), 2.70 (m, 1H), 2.60 (m, 1H) and 1.10 (s, 9H).

EXAMPLE 24

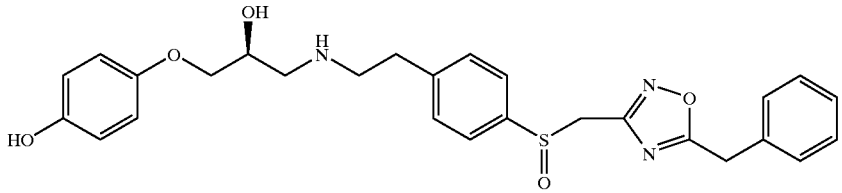

4-({(2S)-3-[(4-{[(5-benzyl-1,2,4-oxadiazol-3-yl)methyl]sulfinyl}phenethyl)amino]-2-hydroxypropyl}oxy)phenol To a solution of the amino alcohol of Example 23 (0.490 g, 0.643 mmol) in THF (10 mL) was added a 1M solution of TBAF (0.13 mL, 0.13 mmol). The reaction mixture was stirred for 6 h. TLC shows the absence of starting material, so 3 drops of a saturated aqueous ammonium chloride solution was added. The reaction mixture was evaporated in vacuo to dryness and the residue was flash chromatographed (silica gel; dichloromethane/chloroform/methanol: 5/4/1) to afford 0.211 g of the title compound as a white crystalline solid. MP=51–57° C.

¹H NMR (400 MHz, DMSO-d₆) δ8.88 (br s, 1H), 7.51 (d, J=8.3 Hz, 2H), 7.40–7.22 (m, 7H), 6.68 (ABq, J=29.2 and 9.0 Hz, 4H), 4.44–4.25 (series of m, 4H), 3.85–3.71 (m, 3H), 2.78 (br s, 4H), 2.69 (m, 1H) and 2.59 (m, 1H).

MS(APCI(+)), [M+H]⁺ @ m/z 508.

Anal: calcd (as hemihydrate); C, 62.77; H, 5.85; N, 8.13 found; C., 62.63; H, 5.98; N, 7.79.

EXAMPLE 25

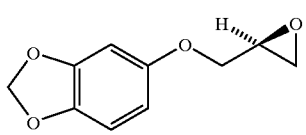

5-[(2S)oxiranylmethoxy]-1,3-benzodioxole

A mixture of sesamol (2.49 g, 18.02 mmol), potassium carbonate (2.74 g, 19.83 mmol) and (2S)-(+)-glycidyl-3-nitrobenzenesulfonate (4.67 g, 18.02 mmol) in 2-butanone (50 mL) was heated to reflux for 18 h. To the cooled reaction mixture was added 35 mL of ethyl acetate and the solids were remove by vacuum filtration. The filtrate was evaporated in vacuo and the residue was taken up into ethyl acetate (65 mL). The solution was washed with aqueous sodium bicarbonate (2×), and water (2×), dried (Na₂SO₄), filtered and evaporated in vacuo. The residue was purified by flash chromatography (silica gel, 50% diethyl ether/hexane) to leave 2.01 g of the title compound.

¹H NMR (300 MHz, CDCl₃) δ6.69 (d, J=8.4 Hz, 1H), 6.52 (d, J=2.5 Hz, 1H), 6.33 (dd, J=8.4 and 2.5 Hz, 1H), 5.91 (s, 2H), 4.14 (ABdd, J=11.0 and 3.3 Hz, 1H), 3.86 (ABdd, J=11.0 and 5.7 Hz, 1H), 3.33 (m, 1H), 2.88 (m, 1H) and 2.74 (m, 1H).

EXAMPLE 26

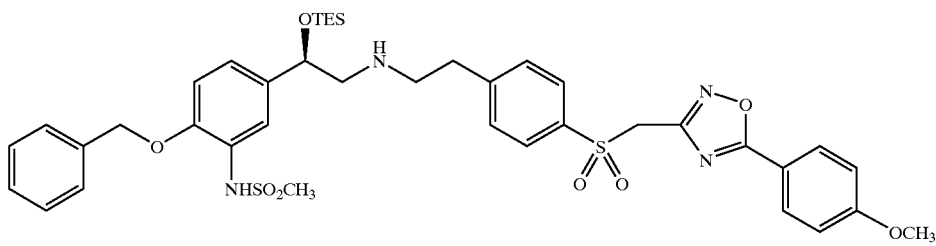

N-(2-(benzyloxy)-5-{(1R)-2-{[4-({[5-(4-methoxyphenyl)-1,2,4-oxadiazol-3-yl]methyl}sulfonyl)phenethyl]amino}-1-[(triethylsilyl)oxy]ethyl}phenyl)methanesulfonamide A solution of the amine of Example 17 (0.90 g, 1.78 mmol), 1(S)-(4-benzyloxy-3-(methylsulfonamido)phenyl-1-triethylsiloxy-2-iodoethane (0.665 g, 1.60 mmol) and triethylamine (0.50 mL, 3.56 mmol) in THF (4 mL) was heated at 100° C. in a sealed tube for 60 h. The reaction mixture was cooled and evaporated in vacuo. The residue was flash chromatographed (silica gel; dichloromethane/ethyl ether/methanol: 25/25/0.75) to yield 0.740 g of the title compound as a white solid.

¹H NMR (300 MHz, CDCl₃) δ8.01 (d, J=8.9 Hz, 2H), 7.80 (d, J=8.3 Hz, 2H), 7.50 (m, 1H), 7.38 (m, 5H), 7.36 (d, J=8.3 Hz, 2H), 7.00 (d, J=8.9 Hz, 2H), 7.03–6.91 (m, 2H), 5.08 (s, 2H), 4.73 (m, 1H), 4.57 (s, 2H), 3.88 (s, 3H), 2.87 (s, 3H), 2.86–2.65 (m, 6H), 0.84 (t, J=7.9 Hz, 9H), and 0.49 (q, J=7.9 Hz, 6H).

MS(ESI(+)), [M+H]⁺ @ m/z 807.

EXAMPLE 27

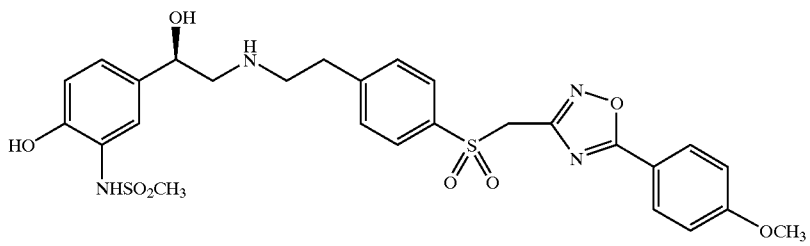

N-[2-hydroxy-5-((1R)-1-hydroxy-2-{[4-({[5-(4-methoxyphenyl)-1,2,4-oxadiazol-3-yl]methyl}sulfonyl)phenethyl]amino}ethyl)phenyl]methanesulfonamide To a solution of the O-protected amino alcohol of Example 26 (0.292 g, 0.362 mmol) in acetonitrile (3 mL) was added 5 equivalents of trimethylsilyl iodide (0.26 mL, 0.1.81 mmol). The reaction mixture was heated to 50° C. for 16 h. TLC shows the absence of starting material, so 1 mL of dilute aqueous sodium bisulfate ($Na_2S_2O_5$) solution was added to the room temperature reaction mixture and it was stirred vigorously for 15 minutes. The reaction mixture was evaporated in vacuo to dryness and the residue was flash chromatographed (silica gel; dichloromethane/chloroform/methanol: 12/3/2) to afford 0.140 g of the title compound as a light yellow crystalline solid.

$^1$H NMR (400 MHz, DMSO-$d_6$) δ9.90 (br, 1H), 8.65 (br, 2H), 7.95 (d, J=8.9 Hz, 2H), 7.84 (d, J=8.3 Hz, 2H), 7.52 (d, J=8.3 Hz, 2H), 7.24 (d, J=2.2 Hz, 1H), 7.15 (d, J=8.9 Hz, 2H), 7.05 (dd, J=8.4 and 2.2 Hz, 1H), 6.88 (d, J=8.4 Hz, 1H), 6.04 (br, 1H), 5.06 (s, 2H), 4.76 (br d, J=9.2 Hz, 1H), 3.85 (s, 3H), 3.30–2.94 (m, 6H) and 2.94 (s, 3H).

MS(ESI(+)), [M+H]$^+$ @ m/z 603.

EXAMPLE 28

(2S)-1-{[4-({[5-(4-methoxyphenyl)-1,2,4-oxadiazol-3-yl]methyl}sulfonyl)phenethyl]amino}-3-{4-[(triisopropylsilyl)oxy]phenoxy}-2-propanol This material was prepared as described in Example 11 from tert-butyl{4-[(2S)oxiranylmethoxy]phenoxy}diphenylsilane (0.45 g, 1.124 mmol) and 4-({[5-(4-methoxyphenyl)-1,2,4-oxadiazol-3-yl]methyl}sulfonyl)phenethylamine (0.70 g, 1.875 mmol). This procedure afforded 0.570 g of the title compound as a white foam.

EXAMPLE 29

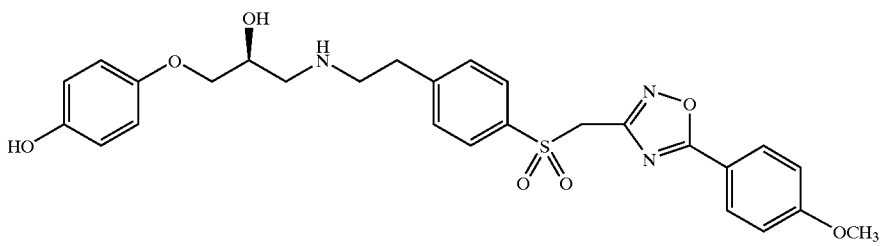

4[((2S)-2-hydroxy-3-{[4-({[5-(4-methoxyphenyl)-1,2,4-oxadiazol-3-yl]methyl}sulfonyl)phenethyl]amino}propyl)oxy]phenol To a solution of the amino alcohol of Example 28(0.57 g, 0.733 mmol) in THF (11 mL) was added a 1M solution of TBAF (0.15 mL, 0.15 mmol). The reaction mixture was stirred for 6 h. TLC shows the absence of starting material, so 3 drops of a saturated aqueous ammonium chloride solution was added. The reaction mixture was evaporated in vacuo to dryness and the residue was flash chromatographed (silica gel; dichloromethane/chloroform/methanol: 6/3/1) to afford 0.240 g of the title compound as a white foam.

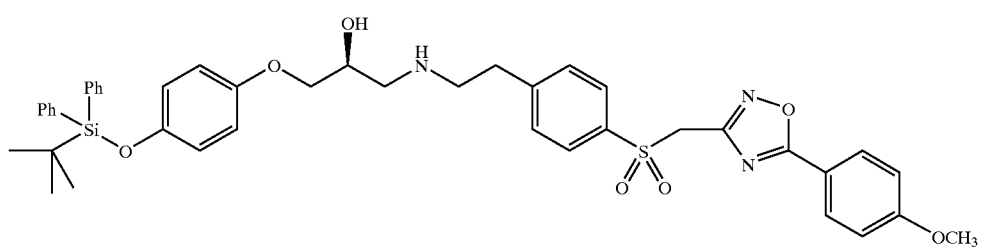

¹H NMR (400 MHz, DMSO-d₆) δ8.87 (br s, 1H), 7.95 (d, J=8.6 Hz, 2H), 7.75 (d, J=8.0 Hz, 2H), 7.48 (d, J=8.0Hz, 2H), 7.14 (d, J=8.6 Hz ,2H), 6.67 (ABq, J=8.8 and 29.2 Hz, 4H), 5.03 (s, 2H), 4.92 (br s, 1H) and 3.85 (s, 3H), 3.80 (m, 3H), 2.81 (m, 4H), 2.64 (m, 1H), and 2.60 (m, 1H).

MS(APCI(+)), [M+H]⁺ @ m/z 540.

Anal: calcd (as hemihydrate); C., 59.11; H, 5.51; N, 7.66 found; C., 59.11; H, 5.44; N, 7.49.

EXAMPLE 30

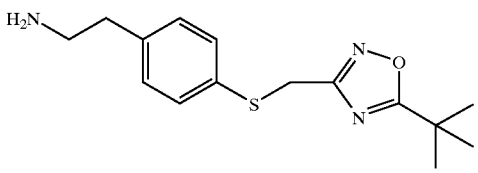

4-({[5-( tert-butyl)-1,2,4-oxadiazol-3-yl]methyl}sulfanyl)phenethylamine

Following the procedures described in Examples 5 and 7 using 3-(chloromethyl)-5-tert-butyl-1,2,4-oxadiazole as alkylating agent afforded the title compound.

MS(ESI(+)), [M+H]⁺ @ m/z 290.

EXAMPLE 31

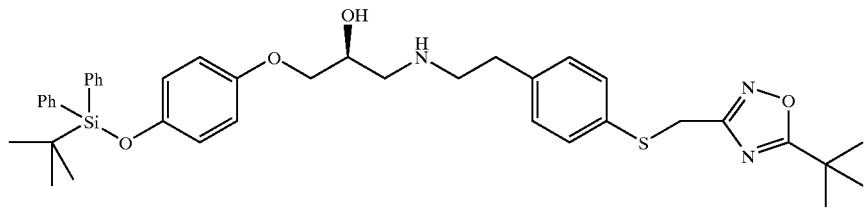

(2S)-1-(4-{[tert-butyl(diphenyl)silyl]oxy}phenoxy)-3-{[4-({[5-(tert-butyl)-1,2,4-oxadiazol-3-yl]methyl}sulfanyl)phenethyl]amino}-2-propanol Following the procedure described in Example 14 using the amine of Example 30 (0.481 g, 1.565 mmol) and tert-butyl{4-[(2S)oxiranylmethoxy]phenoxy}diphenylsilane (0.697 g, 1.721 mmol) afforded 0.140 g of the title compound.

EXAMPLE 32

(2S)-4-(3-{2-[4-(5-tert-Butyl-[1,2,4]oxadiazol-3-ylmethylsulfanyl) -phenyl]-ethylamino}-2-hydroxy-propoxy)-phenol To a solution of the amino alcohol of Example 31(0.140 g, 0.201 mmol) in THF (3 mL) was added a 1M solution of TBAF (0.10 mL, 0.10 mmol). The reaction mixture was stirred for 6 h. TLC showed the absence of starting material, therefore 2 drops of a saturated aqueous ammonium chloride solution was added. The reaction mixture was evaporated in vacuo to dryness and the residue was flash chromatographed (silica gel; dichloromethane/chloroform/methanol: 15/5/3) to afford 0.092 g of the title compound as a tan foam.

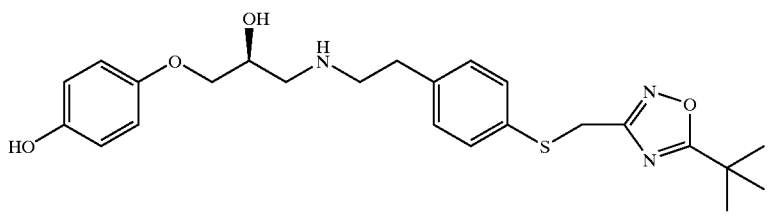

¹H NMR (400 MHz, DMSO-d₆) δ8.90 (s, 1H), 7.30 (d, J=8.1 Hz, 2H), 7.18 (d, J=8.1 Hz, 2H), 6.73 (d, J=9.0 Hz, 2H), 6.66 (d, J=9.0 Hz, 2H), 4.25 (s, 2H), 3.90–3.75 (series of m, 4H), 2.85–2.60 (series of m, 5H), 3.33 (br) and 1.35 (s, 9H).

MS(APCI(+)), [M+H]⁺ @ m/z 458.

Anal: calcd(as hemihydrate); C., 61.78; H, 6.91; N, 9.01 found; C., 61.39; H, 6.24; N, 8.46.

EXAMPLE 33

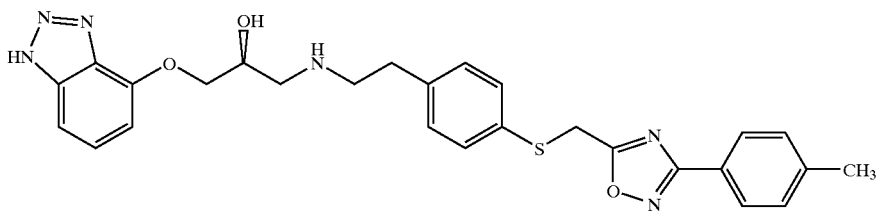

(2S)-1-(1H-1,2,3-benzotriazol-4-yloxy)-3-{[4-({[3-(4-methylphenyl)-1,2,4-oxadiazol-5-yl]methyl}sulfanyl)phenethyl]amino}-2-propanol To a solution of 1-(2,3-diaminophenoxy)-3-[[2-[4-[[[3-(4-methylphenyl)-1,2,4-oxadiazol-5-yl]methyl]thio]phenyl]ethyl]amino]-2-propanol (0.077 g, 0.172 mmol.) in acetic acid (1.2 mL) at 5° C. was added a solution of sodium nitrite (0.013 g, 0.189 mmol) in water (0.5 mL). The mixture was stirred for 30 minutes and evaporated to dryness. The residue was purified by flash chromatography (silica gel; $CH_2Cl_2$/MeOH (3/1) to afford 0.079 g of the pure title compound. MP=110° C.

$^1$H NMR (400 MHz, DMSO-$d_6$) $\delta$7.82 (d, 8.1 Hz, 2H), 7.33 (m, 4H), 7.19 (d, J=8.1 Hz, 2H), 6.81 (d, J=7.4 Hz, 1H), 4.58 (s, 2H), 4.20 (m, 2H), 4.03 (br m, 1H), 2.90–2.70 (series of m, 4H) and 2.35 (s, 3H).

MS(ESI(+)), [M+H]$^+$ @ m/z 517

Anal: calcd(as hydrate); C., 60.66; H, 5.01; N, 15.72 found; C., 60.69; H, 5.28; N, 15.63.

What is claimed is:

1. A compound of formula I having the structure

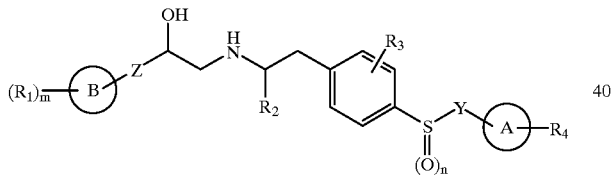

I wherein,

R$_1$ is hydrogen, alkyl of 1–6 carbon atoms, halogen, trifluoromethyl, trifluoromethoxy, alkoxy of 1–6 carbon atoms, hydroxy, nitro, amino, cyano, carboxy, alkoxycarbonyl of 2–7 carbon atoms, aminocarbonyl, alkylamino of 1–6 carbon atoms, dialkylamino of 1–6 carbon atoms per alkyl group, acyl of 2–7 carbon atoms, acylamino of 2–7 carbon atoms, amino, phenylalkyl having 1–6 carbon atoms in the alkyl moiety, or —NR$_5$SO$_2$R$_5$;

R$_2$ is hydrogen, or alkyl of 1–6 carbon atoms;

R$_3$ is hydrogen, alkyl of 1–6 carbon atoms, alkoxy of 1–6 carbon atoms, or halogen;

R$_4$ is (a) a 5–6 membered heterocyclic ring having 1–4 heteroatoms selected from O, S, and N, optionally substituted with R$_6$; (b) a phenyl ring optionally substituted with R$_6$; (c) phenylalkyl having 1–6 carbon atoms in the alkyl moiety; or (d) alkyl of 1–6 carbon atoms;

R$_5$ is hydrogen, alkyl of 1–6 carbon atoms, or phenyl;

R$_6$ is alkyl of 1–6 carbon atoms, halogen, trifluoromethyl, trifluoromethoxy, alkoxy of 1–6 carbon atoms, hydroxy, nitro, amino, cyano, aminocarbonyl, alkylamino of 1–6 carbon atoms, dialkylamino of 1–6 carbon atoms per alkyl group, acyl of 2–7 carbon atoms, acylamino of 2–7 carbon atoms, amino, phenylalkyl having 1–6 carbon atoms in the alkyl moiety, —CO$_2$R$_5$, or —NR$_5$SO$_2$R$_5$; or is a 5–6 membered heterocyclic ring having 1–4 heteroatoms selected from O, S, and N mono- or di- substituted with R$_2$;

is (a) a 5–6 membered heterocyclic ring having 1–4 heteroatoms selected from O, N, and S; or
(b) a phenyl ring;

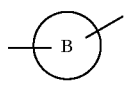

is (a) a phenyl ring; or
(b) a phenyl fused to a 5–membered heterocyclic ring having 1–4 heteroatoms selected from O, N, and S;

Y is alkyl of 1–6 carbon atoms;

Z is a bond, or —OCH$_2$—;

m is 1–2;

with the proviso that

   and   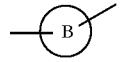

are both not phenyl;

or a pharmaceutically acceptable salt thereof.

2. The compound according to claim 1, wherein

R$_1$ is hydrogen, alkyl of 1–6 carbon atoms, halogen, trifluoromethoxy, alkoxy of 1–6 carbon atoms, hydroxy, cyano, or —NR$_5$SO$_2$R$_5$;

R$_3$ is hydrogen;

R$_6$ is alkyl of 1–6 carbon atoms, alkoxy of 1–6 carbon atoms, or is a 5–6 membered heterocyclic ring having 1–4 heteroatoms selected from O, S, and N mono- or di- substituted with R$_2$;

Y is methylene;

or a pharmaceutically acceptable salt thereof.

3. The compound of claim 1, which is a) 4-(4-{2-[(2S)-3-(1H-Benzotriazol-4-yloxy)-2-hydroxy-propylamino]-ethyl}-phenylsulfanylmethyl)-benzonitrile;

b) (2S)-1-(1H-Benzotriazol-4-yloxy)-3-{2-[4-(3-p-tolyl-[1,2,4]oxadiazol-5-ylmethylsulfanyl)-phenyl]-ethylamino}-propan-2-ol;

c) 4-(3-{2-[4-(5-tert-Butyl-[1,2,4]oxadiazol-3-ylmethylsulfanyl)-phenyl]-ethylamino}-2-hydroxy-propoxy)-phenol;
d) 4-[(2S)-3-(2-{4-[5-(3,5-Dimethyl-isoxazol-4-yl)-[1,2,4]oxadiazol-3-ylmethylsulfanyl]-phenyl}-ethylamino)-2-hydroxy-propoxy]-phenol;
e) 4-((2S)-3-{2-[4-(5-tert-Butyl-[1,2,4]oxadiazol-3-ylmethanesulfonyl)-phenyl]-ethylamino}-2-hydroxy-propoxy)-phenol;
f) 4-[(2S)-2-Hydroxy-3-(2-{4-[5-(4-methoxy-phenyl)-[1,2,4]oxadiazol-3-ylmethylsulfanyl]-phenyl}-ethylamino)-propoxy]-phenol;
g) 4-[(2S)-2-Hydroxy-3-(2-{4-[5-(4-methoxy-phenyl)-[1,2,4]oxadiazol-3-ylmethylsulfanyl]-phenyl}-ethylamino)-propoxy]-2-methyl-phenol;
h) 4-((2S)-3-{2-[4-(5-Benzyl-[1,2,4]oxadiazol-3-ylmethanesulfinyl)-phenyl]-ethylamino}-2-hydroxy-propoxy)-phenol;
i) 2-[(4-{[(5-phenyl-1,2,4-oxadiazol-3-yl)methyl]sulfonyl}phenethyl)amino]-1-[4-(trifluoromethoxy)phenyl]-1-ethanol; or
j) N-[2-hydroxy-5-((1R)-1-hydroxy-2-{[4-({[5-(4-methoxyphenyl)-1,2,4-oxadiazol-3-yl]methyl}sulfonyl)phenethyl]amino}ethyl)phenyl]methane sulfonamide or a pharmaceutically acceptable salt thereof.

4. A method of treating metabolic disorders mediated by insulin resistance or hyperglycemia in a mammal in need thereof which comprises providing to said mammal, an effective amount of a compound of formula I having the structure

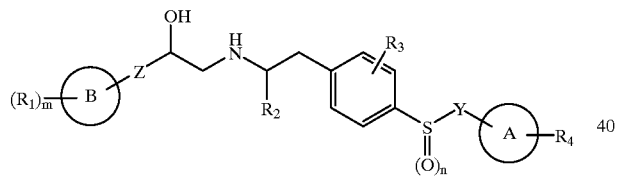

I wherein,
R$_1$ is hydrogen, alkyl of 1–6 carbon atoms, halogen, trifluoromethyl, trifluoromethoxy, alkoxy of 1–6 carbon atoms, hydroxy, nitro, amino, cyano, carboxy, alkoxycarbonyl of 2–7 carbon atoms, aminocarbonyl, alkylamino of 1–6 carbon atoms, dialkylamino of 1–6 carbon atoms per alkyl group, acyl of 2–7 carbon atoms, acylamino of 2–7 carbon atoms, amino, phenylalkyl having 1–6 carbon atoms in the alkyl moiety, or —NR$_5$SO$_2$R$_5$;
R$_2$ is hydrogen, or alkyl of 1–6 carbon atoms;
R$_3$ is hydrogen, alkyl of 1–6 carbon atoms, alkoxy of 1–6 carbon atoms, or halogen;
R$_4$ is (a) a 5–6 membered heterocyclic ring having 1–4 heteroatoms selected from O, S, and N, optionally substituted with R$_6$; (b) a phenyl ring optionally substituted with R$_6$; (c) phenylalkyl having 1–6 carbon atoms in the alkyl moiety; or (d) alkyl of 1–6 carbon atoms;
R$_5$ is hydrogen, alkyl of 1–6 carbon atoms, or phenyl;
R$_6$ is alkyl of 1–6 carbon atoms, halogen, trifluoromethyl, trifluoromethoxy, alkoxy of 1–6 carbon atoms, hydroxy, nitro, amino, cyano, aminocarbonyl, alkylamino of 1–6 carbon atoms, dialkylamino of 1–6 carbon atoms per alkyl group, acyl of 2–7 carbon atoms, acylamino of 2–7 carbon atoms, amino, phenylalkyl having 1–6 carbon atoms in the alkyl moiety, —CO$_2$R$_5$, or —NR$_5$SO$_2$R$_5$; or is a 5–6 membered heterocyclic ring having 1–4 heteroatoms selected from O, S, and N mono- or di- substituted with R$_2$;

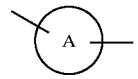

is
(a) a 5–6 membered heterocyclic ring having 1–4 heteroatoms selected from O, N, and S; or
(b) a phenyl ring;

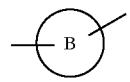

is
(a) a phenyl ring; or
(b) a phenyl fused to a 5–6 membered heterocyclic ring having 1–4 heteroatoms selected from O, N, and S;
Y is alkyl of 1–6 carbon atoms;
Z is a bond, or —OCH$_2$—;
m is 1–2;
n is 0–2;
with the proviso that

 and 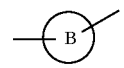

are both not phenyl;
or a pharmaceutically acceptable salt thereof.

5. A method of treating or inhibiting type II diabetes in a mammal in need thereof which comprises providing to said mammal, an effective amount of a compound of Formula I having the structure

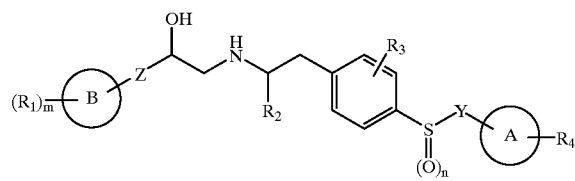

I wherein,
R$_1$ is hydrogen, alkyl of 1–6 carbon atoms, halogen, trifluoromethyl, trifluoromethoxy, alkoxy of 1–6 carbon atoms, hydroxy, nitro, amino, cyano, carboxy, alkoxycarbonyl of 2–7 carbon atoms, aminocarbonyl, alkylamino of 1–6 carbon atoms, dialkylamino of 1–6 carbon atoms per alkyl group, acyl of 2–7 carbon atoms, acylamino of 2–7 carbon atoms, amino, phenylalkyl having 1–6 carbon atoms in the alkyl moiety, or —NR$_5$SO$_2$R$_5$;
R$_2$ is hydrogen, or alkyl of 1–6 carbon atoms;
R$_3$ is hydrogen, alkyl of 1–6 carbon atoms, alkoxy of 1–6 carbon atoms, or halogen;

R₄ is (a) a 5–6 membered heterocyclic ring having 1–4 heteroatoms selected from O, S, and N, optionally substituted with R₆; (b) a phenyl ring optionally substituted with R₆; (c) phenylalkyl having 1–6 carbon atoms in the alkyl moiety; or (d) alkyl of 1–6 carbon atoms;

R₅ is hydrogen, alkyl of 1–6 carbon atoms, or phenyl;

R₆ is alkyl of 1–6 carbon atoms, halogen, trifluoromethyl, trifluoromethoxy, alkoxy of 1–6 carbon atoms, hydroxy, nitro, amino, cyano, aminocarbonyl, alkylamino of 1–6 carbon atoms, dialkylamino of 1–6 carbon atoms per alkyl group, acyl of 2–7 carbon atoms, acylamino of 2–7 carbon atoms, amino, phenylalkyl having 1–6 carbon atoms in the alkyl moiety, —CO₂R₅, or —NR₅SO₂R₅; or is a 5–6 membered heterocyclic ring having 1–4 heteroatoms selected from O, S, and N mono- or di- substituted with R₂;

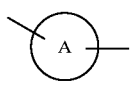

is
(a) a 5–6 membered heterocyclic ring having 1–4 heteroatoms selected from O, N, and S; or
(b) a phenyl ring;
is
(a) a phenyl ring; or
(b) a phenyl fused to a 5–6 membered heterocyclic ring having 1–4 heteroatoms selected from O, N, and S;

Y is alkyl of 1–6 carbon atoms;

Z is a bond, or —OCH₂—;

m is 1–2;

n is 0–2;

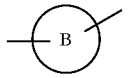

with the proviso

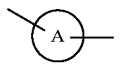 and 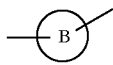

that are both not phenyl;

or a pharmaceutically acceptable salt thereof.

6. A method of modulating glucose levels in a mammal in need thereof which comprises providing to said mammal, an effective amount of a compound of formula I having the structure

I

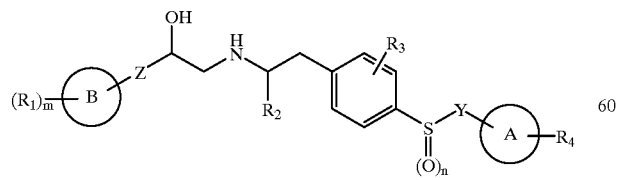

wherein,

R₁ is hydrogen, alkyl of 1–6 carbon atoms, halogen, trifluoromethyl, trifluoromethoxy, alkoxy of 1–6 carbon atoms, hydroxy, nitro, amino, cyano, carboxy, alkoxycarbonyl of 2–7 carbon atoms, aminocarbonyl, alkylamino of 1–6 carbon atoms, dialkylamino of 1–6 carbon atoms per alkyl group, acyl of 2–7 carbon atoms, acylamino of 2–7 carbon atoms, amino, phenylalkyl having 1–6 carbon atoms in the alkyl moiety, or —NR₅SO₂R₅;

R₂ is hydrogen, or alkyl of 1–6 carbon atoms;

R₃ is hydrogen, alkyl of 1–6 carbon atoms, alkoxy of 1–6 carbon atoms, or halogen;

R₄ is (a) a 5–6 membered heterocyclic ring having 1–4 heteroatoms selected from O, S, and N, optionally substituted with R₆; (b) a phenyl ring optionally substituted with R₆; (c) phenylalkyl having 1–6 carbon atoms in the alkyl moiety; or (d) alkyl of 1–6 carbon atoms;

R₅ is hydrogen, alkyl of 1–6 carbon atoms, or phenyl;

R₆ is alkyl of 1–6 carbon atoms, halogen, trifluoromethyl, trifluoromethoxy, alkoxy of 1–6 carbon atoms, hydroxy, nitro, amino, cyano, aminocarbonyl, alkylamino of 1–6 carbon atoms, dialkylamino of 1–6 carbon atoms per alkyl group, acyl of 2–7 carbon atoms, acylamino of 2–7 carbon atoms, amino, phenylalkyl having 1–6 carbon atoms in the alkyl moiety, —CO₂R₅, or —NR₅SO₂R₅; or is a 5–6 membered heterocyclic ring having 1–4 heteroatoms selected from O, S, and N mono- or di- substituted with R₂;

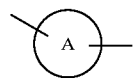

is
(a) a 5–6 membered heterocyclic ring having 1–4 heteroatoms selected from O, N, and S; or
(b) a phenyl ring;

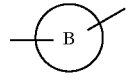

is
(a) a phenyl ring; or
(b) a phenyl fused to a 5–6 membered heterocyclic ring having 1–4 heteroatoms selected from O, N, and S;

Y is alkyl of 1–6 carbon atoms;

Z is a bond, or —OCH₂—;

m is 1–2;

n is 0–2;

with the proviso thant

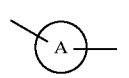 and 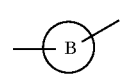

are both not phenyl;

or a pharmaceutically acceptable salt thereof.

7. A method of treating or inhibiting urinary incontinence in a mammal in need thereof which comprises providing to said mammal an effective amount of a compound of formula I having the structure

I

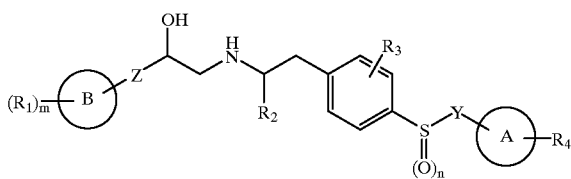

wherein,
- R₁ is hydrogen, alkyl of 1–6 carbon atoms, halogen, trifluoromethyl, trifluoromethoxy, alkoxy of 1–6 carbon atoms, hydroxy, nitro, amino, cyano, carboxy, alkoxycarbonyl of 2–7 carbon atoms, aminocarbonyl, alkylamino of 1–6 carbon atoms, dialkylamino of 1–6 carbon atoms per alkyl group, acyl of 2–7 carbon atoms, acylamino of 2–7 carbon atoms, amino, phenylalkyl having 1–6 carbon atoms in the alkyl moiety, or —NR₅SO₂R₅;
- R₂ is hydrogen, or alkyl of 1–6 carbon atoms;
- R₃ is hydrogen, alkyl of 1–6 carbon atoms, alkoxy of 1–6 carbon atoms, or halogen;
- R₄ is (a) a 5–6 membered heterocyclic ring having 1–4 heteroatoms selected from O, S, and N, optionally substituted with R₆; (b) a phenyl ring optionally substituted with R₆; (c) phenylalkyl having 1–6 carbon atoms in the alkyl moiety; or (d) alkyl of 1–6 carbon atoms;
- R₅ is hydrogen, alkyl of 1–6 carbon atoms, or phenyl;
- R₆ is alkyl of 1–6 carbon atoms, halogen, trifluoromethyl, trifluoromethoxy, alkoxy of 1–6 carbon atoms, hydroxy, nitro, amino, cyano, aminocarbonyl, alkylamino of 1–6 carbon atoms, dialkylamino of 1–6 carbon atoms per alkyl group, acyl of 2–7 carbon atoms, acylamino of 2–7 carbon atoms, amino, phenylalkyl having 1–6 carbon atoms in the alkyl moiety, —CO₂R₅, or —NR₅SO₂R₅; or is a 5–6 membered heterocyclic ring having 1–4 heteroatoms selected from O, S, and N mono- or di- substituted with R₂;

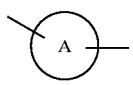

is
(a) a 5–6 membered heterocyclic ring having 1–4 heteroatoms selected from O, N, and S; or
(b) a phenyl ring;

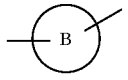

is
(a) a phenyl ring; or
(b) a phenyl fused to a 5–6 membered heterocyclic ring having 1–4 heteroatoms selected from O, N, and S;
Y is alkyl of 1–6 carbon atoms;
Z is a bond, or —OCH₂—;
m is 1–2;
n is 0–2;
or a pharmaceutically acceptable salt thereof.

8. A method of treating or inhibiting atherosclerosis, gastrointestinal disorders, neurogenetic inflammation, glaucoma, or ocular hypertension in a mammal in need thereof, which comprises providing to said mammal an effective amount of a compound of formula I having the structure

I

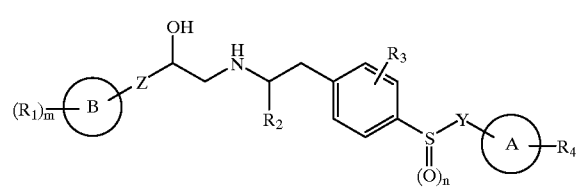

wherein,
- R₁ is hydrogen, alkyl of 1–6 carbon atoms, halogen, trifluoromethyl, trifluoromethoxy, alkoxy of 1–6 carbon atoms, hydroxy, nitro, amino, cyano, carboxy, alkoxycarbonyl of 2–7 carbon atoms, aminocarbonyl, alkylamino of 1–6 carbon atoms, dialkylamino of 1–6 carbon atoms per alkyl group, acyl of 2–7 carbon atoms, acylamino of 2–7 carbon atoms, amino, phenylalkyl having 1–6 carbon atoms in the alkyl moiety, or —NR₅SO₂R₅;
- R₂ is hydrogen, or alkyl of 1–6 carbon atoms;
- R₃ is hydrogen, alkyl of 1–6 carbon atoms, alkoxy of 1–6 carbon atoms, or halogen;
- R₄ is (a) a 5–6 membered heterocyclic ring having 1–4 heteroatoms selected from O, S, and N, optionally substituted with R₆; (b) a phenyl ring optionally substituted with R₆; (c) phenylalkyl having 1–6 carbon atoms in the alkyl moiety; or (d) alkyl of 1–6 carbon atoms;
- R₅ is hydrogen, alkyl of 1–6 carbon atoms, or phenyl;
- R₆ is alkyl of 1–6 carbon atoms, halogen, trifluoromethyl, trifluoromethoxy, alkoxy of 1–6 carbon atoms, hydroxy, nitro, amino, cyano, aminocarbonyl, alkylamino of 1–6 carbon atoms, dialkylamino of 1–6 carbon atoms per alkyl group, acyl of 2–7 carbon atoms, acylamino of 2–7 carbon atoms, amino, phenylalkyl having 1–6 carbon atoms in the alkyl moiety, —CO₂R₅, or —NR₅SO₂R₅; or is a 5–6 membered heterocyclic ring having 1–4 heteroatoms selected from O, S, and N mono- or di- substituted with R₂;

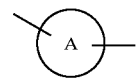

is
(a) a 5–6 membered heterocyclic ring having 1–4 heteroatoms selected from O, N, and S; or
(b) a phenyl ring;

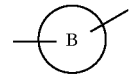

is
(a) a phenyl ring; or
(b) a phenyl fused to a 5–6 membered heterocyclic ring having 1–4 heteroatoms selected from O, N, and S;
Y is alkyl of 1–6 carbon atoms;
Z is a bond, or —OCH₂—;

m is 1–2;

n is 0–2;

or a pharmaceutically acceptable salt thereof.

9. A method of increasing the lean meat to fat ratio in a mammal in need thereof, which comprises providing to said mammal an effective amount of a compound of formula I having the structure

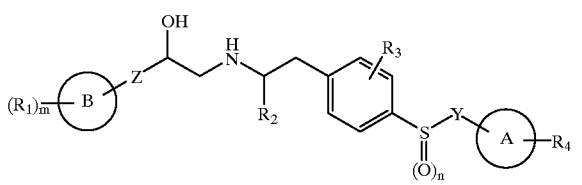

I wherein,

- $R_1$ is hydrogen, alkyl of 1–6 carbon atoms, halogen, trifluoromethyl, trifluoromethoxy, alkoxy of 1–6 carbon atoms, hydroxy, nitro, amino, cyano, carboxy, alkoxycarbonyl of 2–7 carbon atoms, aminocarbonyl, alkylamino of 1–6 carbon atoms, dialkylamino of 1–6 carbon atoms per alkyl group, acyl of 2–7 carbon atoms, acylamino of 2–7 carbon atoms, amino, phenylalkyl having 1–6 carbon atoms in the alkyl moiety, or —$NR_5SO_2R_5$;
- $R_2$ is hydrogen, or alkyl of 1–6 carbon atoms;
- $R_3$ is hydrogen, alkyl of 1–6 carbon atoms, alkoxy of 1–6 carbon atoms, or halogen;
- $R_4$ is (a) a 5–6 membered heterocyclic ring having 1–4 heteroatoms selected from O, S, and N, optionally substituted with $R_6$; (b) a phenyl ring optionally substituted with $R_6$; (c) phenylalkyl having 1–6 carbon atoms in the alkyl moiety; or (d) alkyl of 1–6 carbon atoms;
- $R_5$ is hydrogen, alkyl of 1–6 carbon atoms, or phenyl;
- $R_6$ is alkyl of 1–6 carbon atoms, halogen, trifluoromethyl, trifluoromethoxy, alkoxy of 1–6 carbon atoms, hydroxy, nitro, amino, cyano, aminocarbonyl, alkylamino of 1–6 carbon atoms, dialkylamino of 1–6 carbon atoms per alkyl group, acyl of 2–7 carbon atoms, acylamino of 2–7 carbon atoms, amino, phenylalkyl having 1–6 carbon atoms in the alkyl moiety, —$CO_2R_5$, or —$NR_5SO_2R_5$; or is a 5–6 membered heterocyclic ring having 1–4 heteroatoms selected from O, S, and N mono- or di- substituted with $R_2$;

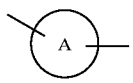

is (a) a 5–6 membered heterocyclic ring having 1–4 heteroatoms selected from O, N, and S; or (b) a phenyl ring;

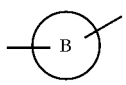

is (a) a phenyl ring; or (b) a phenyl fused to a 5–6 membered heterocyclic ring having 1–4 heteroatoms selected from O, N, and S;

Y is alkyl of 1–6 carbon atoms;

Z is a bond, or —$OCH_2$—;

m is 1–2;

n is 0–2;

or a pharmaceutically acceptable salt thereof.

10. A pharmaceutical composition which comprises a compound of formula I having the structure

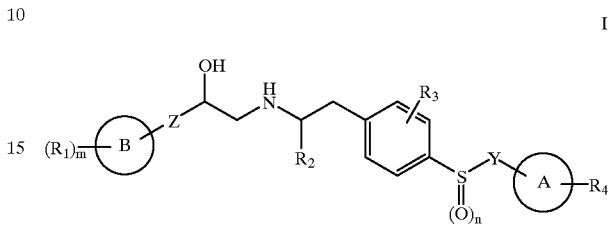

I wherein,

- $R_1$ is hydrogen, alkyl of 1–6 carbon atoms, halogen, trifluoromethyl, trifluoromethoxy, alkoxy of 1–6 carbon atoms, hydroxy, nitro, amino, cyano, carboxy, alkoxycarbonyl of 2–7 carbon atoms, aminocarbonyl, alkylamino of 1–6 carbon atoms, dialkylamino of 1–6 carbon atoms per alkyl group, acyl of 2–7 carbon atoms, acylamino of 2–7 carbon atoms, amino, phenylalkyl having 1–6 carbon atoms in the alkyl moiety, or —$NR_5SO_2R_5$;
- $R_2$ is hydrogen, or alkyl of 1–6 carbon atoms;
- $R_3$ is hydrogen, alkyl of 1–6 carbon atoms, alkoxy of 1–6 carbon atoms, or halogen;
- $R_4$ is (a) a 5–6 membered heterocyclic ring having 1–4 heteroatoms selected from O, S, and N, optionally substituted with $R_6$; (b) a phenyl ring optionally substituted with $R_6$; (c) phenylalkyl having 1–6 carbon atoms in the alkyl moiety; or (d) alkyl of 1–6 carbon atoms;
- $R_5$ is hydrogen, alkyl of 1–6 carbon atoms, or phenyl;
- $R_6$ is alkyl of 1–6 carbon atoms, halogen, trifluoromethyl, trifluoromethoxy, alkoxy of 1–6 carbon atoms, hydroxy, nitro, amino, cyano, aminocarbonyl, alkylamino of 1–6 carbon atoms, dialkylamino of 1–6 carbon atoms per alkyl group, acyl of 2–7 carbon atoms, acylamino of 2–7 carbon atoms, amino, phenylalkyl having 1–6 carbon atoms in the alkyl moiety, —$CO_2R_5$, or —$NR_5SO_2R_5$; or is a 5–6 membered heterocyclic ring having 1–4 heteroatoms selected from O, S, and N mono- or di- substituted with $R_2$;

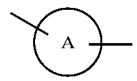

is (a) a 5–6 membered heterocyclic ring having 1–4 heteroatoms selected from O, N, and S; or (b) a phenyl ring;

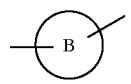

is
(a) a phenyl ring; or
(b) a phenyl fused to a 5–6 membered heterocyclic ring having 1–4 heteroatoms selected from O, N, and S;
Y is alkyl of 1–6 carbon atoms;
Z is a bond, or —OCH$_2$—;
m is 1–2;
n is 0–2;
with the proviso that
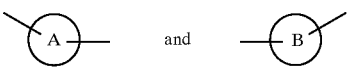
are both not phenyl;
or a pharmaceutically acceptable salt thereof, and a pharmaceutical carrier.
* * * * *